United States Patent
Kimoto et al.

(10) Patent No.: US 8,038,599 B2
(45) Date of Patent: Oct. 18, 2011

(54) WIRELESS IN-VIVO INFORMATION ACQUIRING APPARATUS, WIRELESS IN-VIVO INFORMATION ACQUIRING SYSTEM, AND COMMUNICATION APPARATUS

(75) Inventors: Seiichiro Kimoto, Tokyo (JP); Takeshi Mori, Tokyo (JP); Noriyuki Fujimori, Nagano (JP)

(73) Assignee: Olympus Corporation (JP)

(*) Notice: Subject to any disclaimer, the term of this patent is extended or adjusted under 35 U.S.C. 154(b) by 1231 days.

(21) Appl. No.: 11/569,937

(22) PCT Filed: Mar. 30, 2005

(86) PCT No.: PCT/JP2005/006176
§ 371 (c)(1),
(2), (4) Date: Feb. 6, 2007

(87) PCT Pub. No.: WO2005/117682
PCT Pub. Date: Dec. 15, 2005

(65) Prior Publication Data
US 2009/0163771 A1    Jun. 25, 2009

(30) Foreign Application Priority Data
Jun. 1, 2004    (JP) .................................. 2004-162986

(51) Int. Cl.
*A61B 1/00* (2006.01)
*A61B 5/07* (2006.01)
(52) U.S. Cl. ...................................... 600/118; 600/302
(58) Field of Classification Search .................. 128/899, 128/903; 600/302
See application file for complete search history.

(56) References Cited

U.S. PATENT DOCUMENTS

| | | | |
|---|---|---|---|
| 6,443,891 B1 * | 9/2002 | Grevious | 600/302 |
| 6,993,358 B2 * | 1/2006 | Shiotsu et al. | 455/552.1 |
| 7,118,531 B2 * | 10/2006 | Krill | 600/309 |
| 2001/0035902 A1 | 11/2001 | Iddan et al. | 348/76 |

(Continued)

FOREIGN PATENT DOCUMENTS
AU    1409701 A    5/2001
(Continued)

OTHER PUBLICATIONS

International Search Report PCT/JP2005/006176 dated Jun. 9, 2005 (Japanese Patent Office).
Search Report issued by European Patent Office on Jun. 7, 2010 in connection with corresponding application No. EP 05 72 1674.

*Primary Examiner* — John P Leubecker
(74) *Attorney, Agent, or Firm* — Ostrolenk Faber LLP

(57) ABSTRACT

A communication apparatus (3) arranged outside a subject (1) has an external device (32) which sequentially transmits control signals. A capsule endoscope (2) is introduced inside the subject (1). Thereafter, a system control circuit controls a driving of an intra-capsule function executing circuit so as to start driving at a previously set given time, by supplying driving power to the intra-capsule function executing circuit to control the driving thereof based on a result of detection by a control-signal detecting circuit which is provided in the capsule endoscope (2) and which detects a discontinuous state of input of the control signals. Thus, a collection and transmission of images inside the subject can be performed accurately.

In addition, a transmitting unit generates and transmits a communication confirmation signal to the communication apparatus. In response, a receiving unit receives a communication permission signal from the communication apparatus. A communication controller determines whether to transmit in-vivo information or not based on the state of reception of the communication permission signal.

20 Claims, 19 Drawing Sheets

U.S. PATENT DOCUMENTS

| | | |
|---|---|---|
| 2002/0198470 A1 | 12/2002 | Imran et al. |
| 2003/0020810 A1 | 1/2003 | Takizawa et al. |
| 2003/0149459 A1* | 8/2003 | Von Arx et al. ............... 607/60 |
| 2003/0172940 A1* | 9/2003 | Rogers et al. ................. 128/899 |
| 2003/0181788 A1 | 9/2003 | Yokoi et al. |
| 2003/0213495 A1 | 11/2003 | Fujita et al. ................... 128/899 |
| 2004/0111011 A1* | 6/2004 | Uchiyama et al. ............ 600/160 |
| 2004/0215084 A1* | 10/2004 | Shimizu et al. ............... 600/476 |
| 2005/0004473 A1* | 1/2005 | Fujita et al. ................... 600/476 |
| 2005/0096562 A1* | 5/2005 | Delalic et al. ................. 600/561 |
| 2005/0227615 A1* | 10/2005 | Sakoda ............................ 455/7 |
| 2005/0256417 A1* | 11/2005 | Fischell et al. ................ 600/510 |

FOREIGN PATENT DOCUMENTS

| | | |
|---|---|---|
| JP | 01-305925 | 12/1989 |
| JP | 04-109927 | 4/1992 |
| JP | 2003-325439 A | 11/2003 |
| JP | 2003-325440 A | 11/2003 |
| JP | 2004-290563 A | 10/2004 |
| JP | 2005-80843 A | 3/2005 |
| JP | 2005-103147 A | 4/2005 |
| WO | WO 01/35813 A1 | 5/2001 |

* cited by examiner

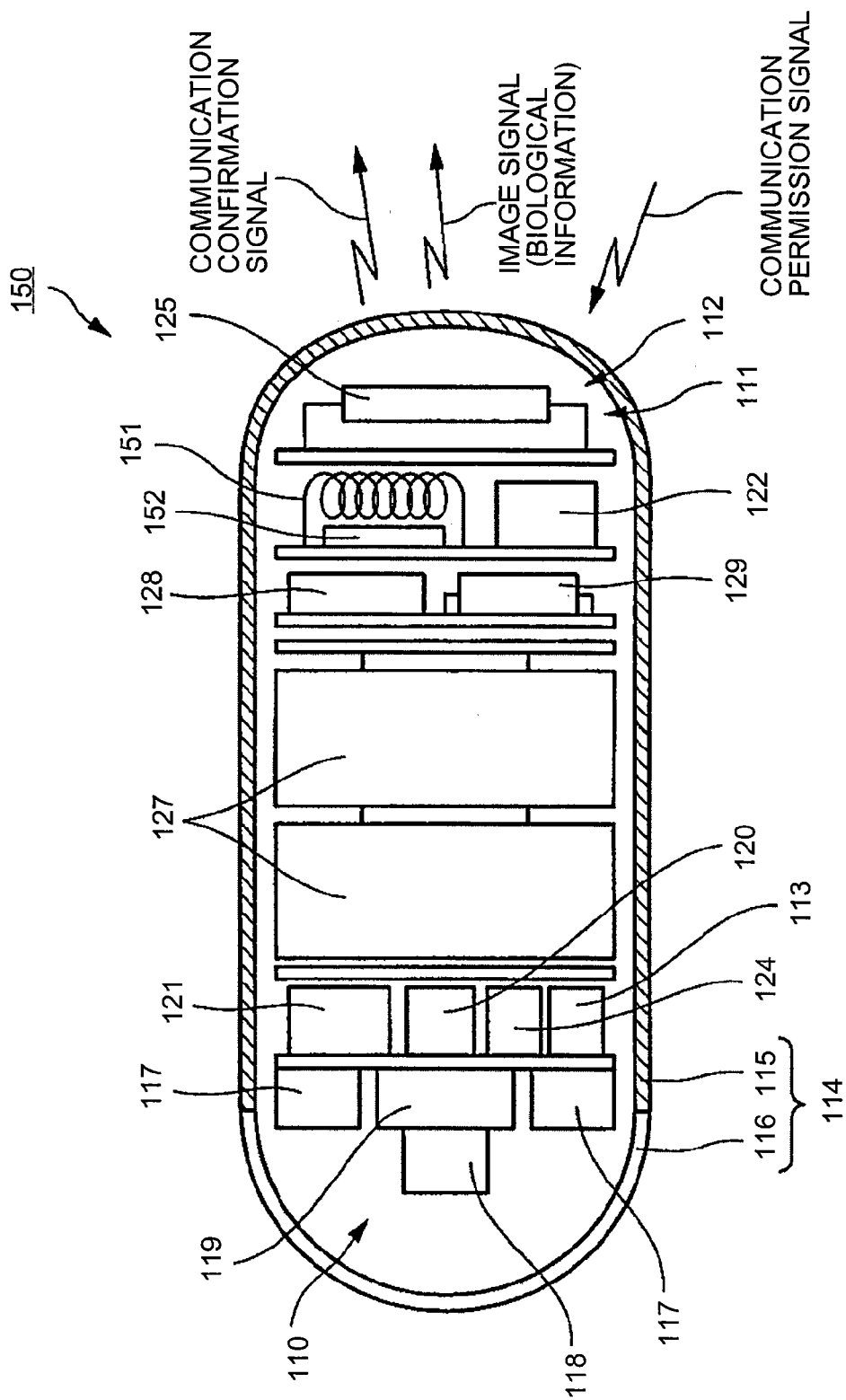

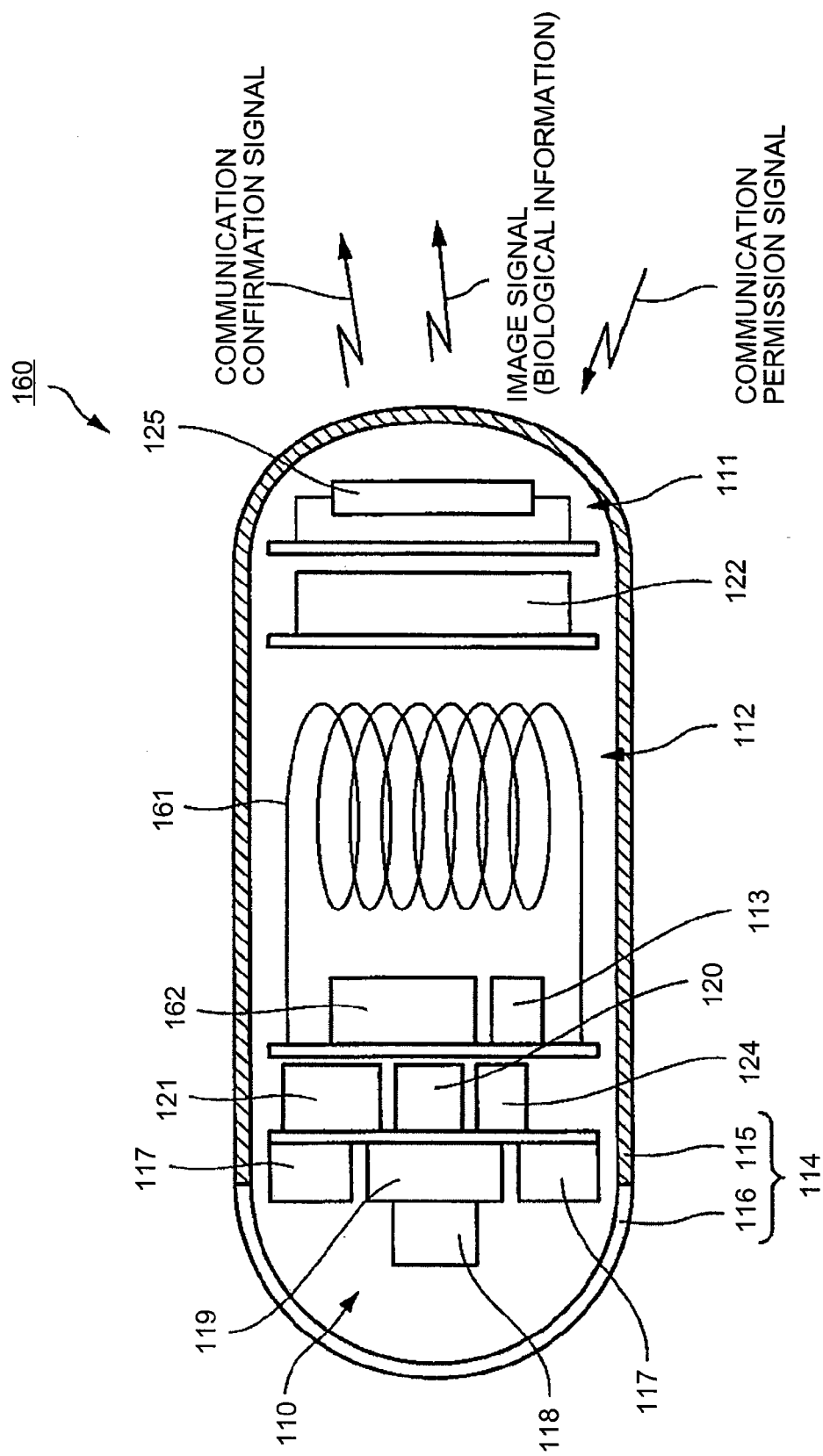

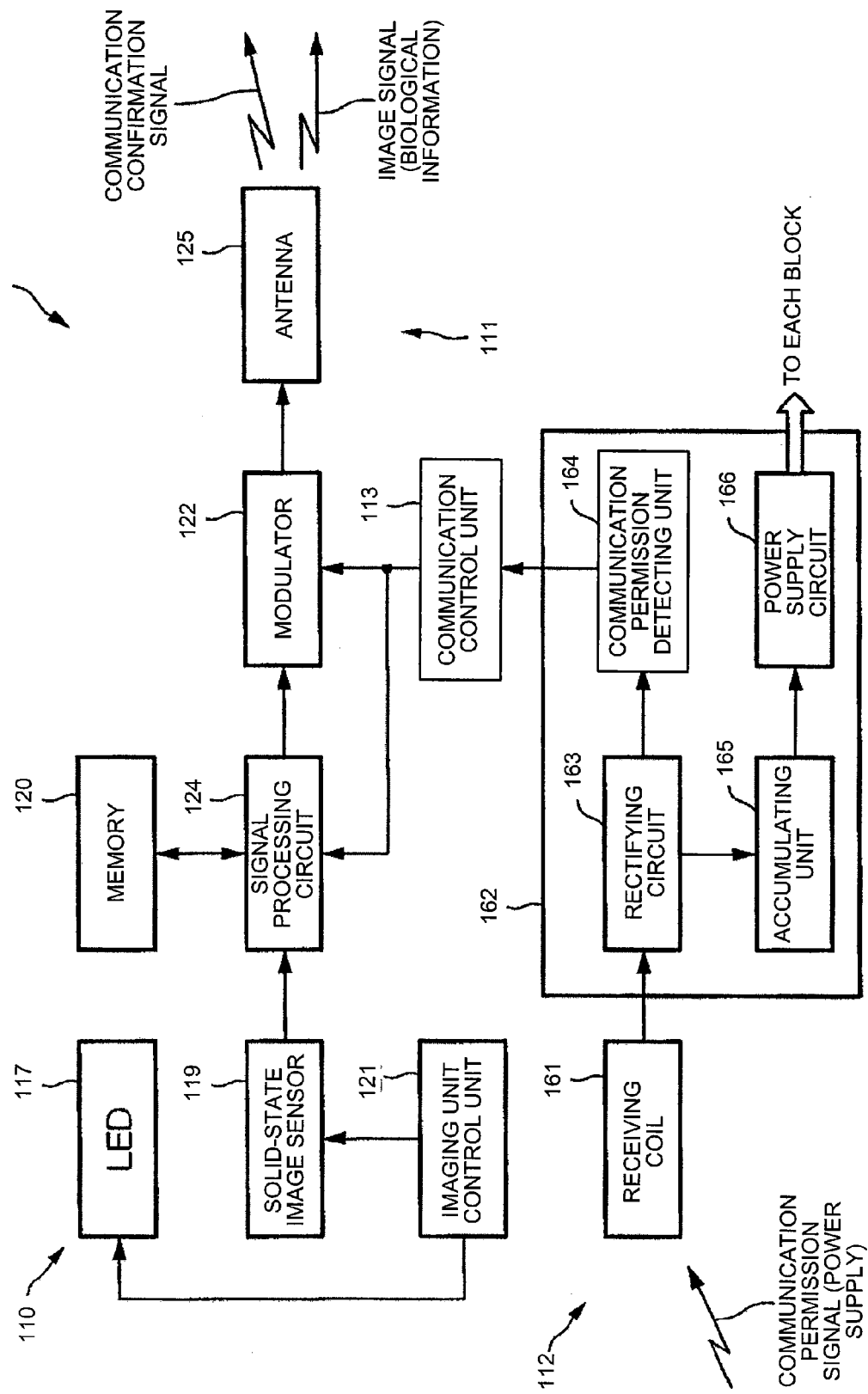

WIRELESS IN-VIVO INFORMATION ACQUIRING APPARATUS, WIRELESS IN-VIVO INFORMATION ACQUIRING SYSTEM, AND COMMUNICATION APPARATUS

CROSS REFERENCE TO RELATED APPLICATION

The present application is a 35 U.S.C. §§371 national phase conversion of PCT/JP2005/006176, filed 30 Mar. 2005, which claims priority of Japanese Patent Application No.2004-162986 filed 1 Jun. 2004, which is herein incorporated by reference. The PCT International Application was published in the Japanese language.

TECHNICAL FIELD

The present invention relates to a wireless in-vivo information acquiring apparatus (capsule-type medical apparatus), a wireless in-vivo information acquiring system (capsule-type communication system), and a communication apparatus (biological information receiving apparatus), and in which power is supplied to each part of the in-vivo information acquiring apparatus, such as a swallowable capsule endoscope, which is introduced into a subject. In particular, the present invention relates to a wireless in-vivo information acquiring apparatus, wireless in-vivo information acquiring system, and a communication apparatus, that regulate timing of power supply to the wireless apparatus.

BACKGROUND ART

In recent years, a capsule endoscope appears in the field of endoscope. The capsule endoscope is equipped with an imaging function and a radio communication function. The capsule endoscope is swallowed by a subject for an observation (examination). After being swallowed, the capsule endoscope moves through inside internal organs (body cavities), such as a stomach and a small intestine, following a peristaltic motion inside the subject, and sequentially picks up images inside using the imaging function until being naturally discharged from a living body of the subject (human body).

While moving inside the internal organs, i.e., during an observation period, the capsule endoscope sequentially transmits data of the picked-up images of the body cavities to an external device placed outside the subject, using the radio function, e.g., by radio communication. The transmitted data is stored in a memory inside the external device. After swallowing the capsule endoscope, the subject carries the external device which has radio communication function and memory function until the capsule endoscope is discharged, whereby the subject can move freely. After the observation, a doctor or a nurse can retrieve the image data stored in the memory of the external device and watch images inside the body cavities on a monitor of a display device, for example, to make diagnosis (see Patent Document 1).

Some of the above described types of the capsule endoscopes are swallowable as described in Patent Document 1. One such proposed capsule endoscope includes a lead switch, which is turned on and off in response to an external magnetic field, in order to control driving of the capsule endoscope. The capsule endoscope is housed inside a package together with a permanent magnet which supplies the external magnetic field. The lead switch provided in the capsule endoscope remains in an off-state in the presence of a magnetic field of a predetermined strength, whereas the lead switch is turned on when the strength of the external magnetic field decreases. Hence, while housed inside the package, the capsule endoscope is not driven. When the subject is to swallow the capsule endoscope, he/she takes out the capsule endoscope from the package. Then, being taken away from the permanent magnet and freed from an influence of the magnetic force, the capsule endoscope starts to be driven. When the capsule endoscope has such a structure, the capsule endoscope is prevented from being driven while remaining inside the package. Once the capsule endoscope is taken out of the package, the capsule endoscope starts picking up images by the imaging function and transmitting image signals by the radio communication function.

Further, some capsule endoscopes as described in Patent Documents 2 and 3, for example, have imaging function and radio communication function similarly to the capsule endoscope of Patent Document 1. Once swallowed by the subject and placed inside the subject, the capsule endoscope advances inside the subject following peristaltic movements of alimentary tract. At the same time, the capsule endoscope picks up images at a fixed frame rate and radio transmits the intra-subject images. The intra-subject images as transmitted are received by a communication apparatus attached to the subject and recorded therein. After the capsule endoscope is discharged, the doctor or a nurse downloads the image data stored in the communication apparatus to a workstation, and makes diagnosis based on the intra-subject images displayed on a monitor of the workstation.

In the conventional capsule endoscopes, radio signals are transmitted only in one direction (uni-directional). Generally, the capsule endoscope only has a transmitting function, while the communication apparatus only has a receiving function. Regardless of a reception status of the communication apparatus, the capsule endoscope continues to radio transmit image signals once placed inside the subject.

Patent Document 1: International Publication WO 01/35813 pamphlet
Patent Document 2: Japanese Patent Application Laid-Open H1-305925 (Kokai)
Patent Document 3: Japanese Patent Application Laid-Open H4-109927 (Kokai)

DISCLOSURE OF INVENTION

Problem to be Solved by the Invention

When the capsule endoscope is structured as described above, however, it takes some time after the capsule endoscope is taken out from the package until placed inside the subject. Therefore, the capsule endoscope starts to be driven before introduced into the subject. When driving starts, the capsule endoscope starts to capture images by the imaging function and radio transmits image signals acquired by image pickup by the radio function. Therefore, if the capsule endoscope is driven before the introduction into the subject, the capsule endoscope ends up performing the imaging operation outside the subject. Then, the capsule endoscope ends up acquiring and radio transmitting image signals that are not necessary for diagnosis.

An imaging rate of the capsule endoscope is set approximately to two frames per second, for example. Even if it takes only about a few tens seconds until the capsule endoscope is placed inside the subject after the package is opened, the capsule endoscope ends up acquiring a large amount of unnecessary image data by operating outside the subject. Therefore, the doctor or the like needs to remove unnecessary image data through a complicated procedure and to extract the image data captured inside the living body before making diagnosis. Thus, it is desirable to prevent the capsule endoscope from being driven before the introduction into the subject, thereby to prevent an acquirement of unnecessary image data.

Further, for acquiring image data, the capsule endoscope needs a certain amount of driving power. Therefore, when the capsule endoscope starts to be driven outside the subject and acquires unnecessary image data, accumulated power inside the capsule endoscope is wasted. Hence, for consumption power saving, it is desirable to prevent the capsule endoscope from being driven before the introduction into the subject.

Still further, sometimes it may be desirable to delay the driving of the capsule endoscope even after the capsule endoscope is introduced into the subject. For example, if the operator wants to acquire image data of a small intestine among various internal organs inside the subject, the operator does not need images of esophagus, stomach, or the like that are located in a passage leading to the small intestine. Then, it may be preferable to start driving the capsule endoscope only after the capsule endoscope reaches the small intestine. In other words, it may be appropriate to selectively drive the capsule endoscope depending on an examined region. Therefore, more preferably, the capsule endoscope is driven only after reaching the examined region, and not immediately after the introduction inside the subject.

Still further, the conventional capsule endoscope transmits radio signals from inside the subject regardless of a reception status of the communication apparatus. When the capsule endoscope transmits data to the communication apparatus which has not established a good communication status with the capsule endoscope, the transmitted data may not be received and become wasted. Such an unnecessary transmission may result in a shorter effective life of the capsule endoscope, i.e., may make the capsule endoscope capable of transmitting receivable data for a shorter time period.

Still further, in a conventional capsule endoscope system, if the capsule endoscope transmits image data while the reception status of the communication apparatus is not good, the communication apparatus cannot store such image data. Then, the doctor or the like cannot make diagnosis for such period.

The present invention is achieved in view of the foregoing, and an object of the present invention is to provide a wireless in-vivo information acquiring apparatus, a wireless in-vivo information acquiring system, and a communication apparatus, according to which the wireless in-vivo information acquiring apparatus is started to be driven at a previously set given time, and collection and transmission of images inside the subject can be securely performed.

Further, another object of the present invention is to provide a wireless in-vivo information acquiring apparatus, a wireless in-vivo information acquiring system, and a communication apparatus that perform the transmission of in-vivo information only when the communication status between a capsule endoscope and the communication apparatus is good.

Means for Solving Problem

A wireless in-vivo information acquiring apparatus according to one aspect of the present invention includes a function executing unit that executes a predetermined function in a subject in which the wireless in-vivo information acquiring apparatus is introduced; a radio receiving unit that is configured to receive a radio signal which is transmitted from outside the subject; and an activating unit that controls an activation of the function executing unit according to a discontinuation in an input of control signals received by the radio receiving unit.

In the wireless in-vivo information acquiring apparatus, the activating unit may determine that the input of the control signals is discontinued when an input level of the control signal received by the radio receiving unit is equal to or lower than a predetermined level, to control the activation of the function executing unit.

In the wireless in-vivo information acquiring apparatus, the radio receiving unit may receive the control signal that is sent from outside the subject and that is within a predetermined frequency band, and the activating unit may detect the control signal that is within the predetermined frequency band and received by the radio receiving unit, and determine that the input of the control signals is discontinued when the input level of the control signal is equal to or lower than a predetermined level, to control the activation of the function executing unit.

In the wireless in-vivo information acquiring apparatus, the activating unit may activate the function executing unit after a predetermined time passes since the control signal is input.

In the wireless in-vivo information acquiring apparatus, the function executing unit may include at least an acquiring unit that acquires in-vivo information, and a radio transmitting unit that transmits the in-vivo information acquired by the acquiring unit to an outside by radio.

A wireless in-vivo information acquiring apparatus according to another aspect of the present invention includes a function executing unit that executes a predetermined function in a subject in which the wireless in-vivo information acquiring apparatus is introduced; a radio receiving unit that is configured to receive a radio signal sent from outside the subject; and an activating unit that controls an activation of the function executing unit according to an input of an activating signal received by the radio receiving unit.

In the wireless in-vivo information acquiring apparatus, the activating unit may control the activation of the function executing unit based on an input level of the activating signal received by the radio receiving unit.

In the wireless in-vivo information acquiring apparatus, the activating unit may control the activation of the function executing unit according to an input of a signal that indicates a command to start activation and that is received from the radio receiving unit.

In the wireless in-vivo information acquiring apparatus, the activating unit may activate the function executing unit after a predetermined time passes since the activating signal is input.

In the wireless in-vivo information acquiring apparatus, the function executing unit may include at least an acquiring unit that acquires in-vivo information, and a radio transmitting unit that transmits the in-vivo information acquired by the acquiring unit to an outside by radio.

A wireless in-vivo information acquiring apparatus according to still another aspect of the present invention detects in-vivo information (biological information) of a subject and transmits the in-vivo information to a communication apparatus located outside the subject. The wireless in-vivo information acquiring apparatus also includes an acquiring unit that acquires the in-vivo information; a transmitting unit that transmits the in-vivo information acquired and a communication confirmation signal to the communication apparatus, the communication confirmation signal serving to confirm a communication status between the wireless in-vivo information acquiring apparatus and the communication apparatus; a receiving unit that receives a radio signal which is sent from the communication apparatus in response to the communication confirmation signal and which includes at least a communication permission signal; and a communication controller that determines whether to transmit the in-vivo information or not based on a state of reception of the communication permission signal. Once the wireless in-vivo information acquiring apparatus according to this invention is introduced into the subject, the wireless in-vivo information acquiring apparatus moves through inside the subject (following peristaltic movements or the like) acquiring the in-vivo information by the acquiring unit. In addition, while the wireless in-vivo information acquiring apparatus moves through the subject and acquires the in-vivo information, the transmitting unit transmits the communication confirmation signal towards outside the subject. On receiving the communication confirmation signal, the communication apparatus transmits the radio signals including the communication permission signal. While the wireless in-vivo information acquiring apparatus moves through the subject, if the receiving unit receives the communication permission signal sent from the communication apparatus, the communication control unit determines whether to transmit the in-vivo information or not based on the reception status of the communication permission signal. If the communication control unit determines to send the communication permission signal, the communication control unit makes the transmitting unit send the in-vivo information. Thus, the wireless in-vivo information acquiring apparatus can transmit the in-vivo information (data) when the communication status between the wireless in-vivo information acquiring apparatus and the communication apparatus is good. Therefore, the wireless in-vivo information acquiring apparatus does not transmit the images in vain while the communication status is not good, i.e., when the communication apparatus is unable to receive the in-vivo information, whereby the power is not consumed in vain. In addition, since the wireless in-vivo information acquiring apparatus transmits the in-vivo information, e.g. plural frames of images while the communication status is good, the communication apparatus does not lose the images. Therefore, more accurate in-vivo information can be acquired.

In the wireless in-vivo information acquiring apparatus, the transmitting unit and the receiving unit may share a same antenna. In the wireless in-vivo information acquiring apparatus, the transmitting unit and the receiving unit may share the same antenna by switching, for example. Thus, the structure of the wireless in-vivo information acquiring apparatus can be simplified and the apparatus as a whole can be downsized.

In the wireless in-vivo information acquiring apparatus, the receiving unit may include an envelope detecting circuit. In the wireless in-vivo information acquiring apparatus, a main part of the receiving unit, for example, main part of a demodulating portion can be formed with passive units. Therefore, the power consumption of the receiving unit can be suppressed. In particular, when the wireless in-vivo information acquiring apparatus employs an embedded battery or the like as a power source, the life of the wireless in-vivo information acquiring apparatus can be prolonged since the battery power consumption can be reduced and the limited power can be efficiently used.

In the wireless in-vivo information acquiring apparatus, the receiving unit may include a rectifying circuit that serves to acquire power from the radio signal, and a communication permission detector that detects the communication permission signal from an output of the rectifying circuit and sends the communication permission signal to the communication controller.

A wireless in-vivo information acquiring system according to still another aspect of the present invention, a wireless in-vivo information acquiring apparatus which is introduced into a subject, and; a communication apparatus which is arranged outside the subject and acquires information acquired by the wireless in-vivo information acquiring apparatus through radio communication. The wireless in-vivo information acquiring apparatus includes a function executing unit that executes a predetermined function in the subject in which the wireless in-vivo information acquiring apparatus is introduced; a radio receiving unit that is configured to receive a radio signal from outside the subject; and an activating unit that controls an activation of the function executing unit according to a discontinuation in an input of control signals received by the radio receiving unit. The communication apparatus includes a radio receiving unit that receives the information transmitted through radio communication; and a radio transmitting unit that transmits the control signal of a predetermined output level through radio communication.

In the wireless in-vivo information acquiring system, the activating unit may determine that the input of the control signals is discontinued when an input level of the control signal from the radio receiving unit is equal to or lower than a predetermined level, to control the activation of the function executing unit.

In the wireless in-vivo information acquiring system, the radio transmitting unit of the communication apparatus may transmit the control signal that is within a predetermined frequency band, the radio receiving unit of the wireless in-vivo information acquiring apparatus may receive the control signal within the predetermined frequency band from outside the subject, and the activating unit may determine that the input of the control signals is discontinued when an input level of the control signal that is within the predetermined frequency band and received by the radio receiving unit is equal to or lower than a predetermined level, to control the activation of the function executing unit.

In the wireless in-vivo information acquiring system, the activating unit may activate the function executing unit after a predetermined time passes since the discontinuation in the input of the control signals.

A wireless in-vivo information acquiring system according to still another aspect of the present invention includes a wireless in-vivo information acquiring apparatus that is introduced inside a subject; and a communication apparatus that is arranged outside the subject and acquires information acquired by the wireless in-vivo information acquiring apparatus by radio communication. The wireless in-vivo information acquiring apparatus includes a function executing unit that executes a predetermined function inside the subject in which the wireless in-vivo information acquiring apparatus is introduced; a radio receiving unit that is configured to receive a radio signal from outside the subject; and an activating unit that controls an activation of the function executing unit according to an input of an activating signal received by the radio receiving unit. The communication apparatus includes a radio receiving unit that receives the information transmitted through radio communication; and a radio transmitting unit that transmits the activating signal through radio communication.

In the wireless in-vivo information acquiring system, the activating unit may control the activation of the function executing unit based on an input level of the activating signal received by the radio receiving unit.

In the wireless in-vivo information acquiring system, the activating unit may control the activation of the function executing unit according to an input of a signal that indicates a command to start activation and that is received by the radio receiving unit.

In the wireless in-vivo information acquiring system, the activating unit may activate the function executing unit after a predetermined time passes since the signal is input.

A wireless in-vivo information acquiring system according to still another aspect of the present invention includes a wireless in-vivo information acquiring apparatus that transmits in-vivo information of a subject from inside the subject to outside the subject; and a communication apparatus that is located outside the subject and receives the in-vivo information, the wireless in-vivo information acquiring system detecting the in-vivo information. The wireless in-vivo information acquiring apparatus transmits a communication confirmation signal to confirm a communication status between the wireless in-vivo information acquiring apparatus and the communication apparatus, the communication apparatus, on receiving the communication confirmation signal, transmits a communication permission signal to permit communication, and the wireless in-vivo information acquiring apparatus includes a communication controller that transmits the in-vivo information on receiving the communication permission signal. In the wireless in-vivo information acquiring system according to this invention, the wireless in-vivo information acquiring apparatus transmits a communication confirmation signal to confirm a communication status between the wireless in-vivo information acquiring apparatus and the communication apparatus, the communication apparatus, on receiving the communication confirmation signal, transmits a communication permission signal to permit the communication, and the wireless in-vivo information acquiring apparatus includes a communication control unit that transmits the in-vivo information on receiving the communication permission signal. In the wireless in-vivo information acquiring system according to the above described aspect of the present invention, the wireless in-vivo information acquiring apparatus transmits the in-vivo information on receiving the communication permission signal sent from the communication apparatus. Therefore, the in-vivo information (data) can be transmitted while the communication status between the wireless in-vivo information acquiring apparatus and the communication apparatus is good. Therefore, the wireless in-vivo information acquiring apparatus does not transmit the images in vain while the communication status is not good, i.e., while the communication apparatus is unable to receive the in-vivo information, whereby the power is not consumed in vain. Further, since the in-vivo information, e.g. plural frames of images are transmitted while the communication status is good, the communication apparatus fails to receive less images, and efficiently receives the in-vivo information. Therefore, more accurate in-vivo information can be acquired.

In the wireless in-vivo information acquiring system according to still another aspect of the present invention, the communication permission signal may also serve as a radio signal for supplying power to the wireless in-vivo information acquiring apparatus. In the wireless in-vivo information acquiring system, the wireless in-vivo information acquiring apparatus can receive power supply via the communication permission signal from the communication apparatus which is arranged outside the subject. Therefore, power exhaustion, such as battery exhaustion can be prevented. Thus, the in-vivo information can be securely acquired.

A communication apparatus (biological information receiving apparatus) according to still another aspect of the present invention is located outside a subject to receive in-vivo information which is transmitted from a wireless in-vivo information acquiring apparatus inside the subject, and to receive a communication confirmation signal which serves to confirm a communication status between the communication apparatus and the wireless in-vivo information acquiring apparatus. The communication apparatus includes a receiving unit that receives the in-vivo information and the communication confirmation signal; a recording unit that records the in-vivo information received; a communication permission signal generator that generates a communication permission signal for permitting the wireless in-vivo information acquiring apparatus to transmit the in-vivo information, when the receiving unit receives the communication confirmation signal; and a communication permission signal transmitting unit that transmits the communication permission signal. In the communication apparatus according to this invention, when the receiving unit receives the communication confirmation signal from the wireless in-vivo information acquiring apparatus inside the subject, the communication-permission-signal generating unit generates the communication permission signal to permit the transmission of the in-vivo information. In other words, the communication-permission-signal generating unit determines that the communication status between the communication apparatus and the wireless in-vivo information acquiring apparatus is good when receiving the communication confirmation signal, and generates the communication permission signal. Then, the communication permission signal transmitting unit transmits the communication permission signal to the wireless in-vivo information acquiring apparatus. On receiving the communication permission signal, the wireless in-vivo information acquiring apparatus transmits the in-vivo information. The in-vivo information is received by the receiving unit and recorded in the recording unit. Thus, the communication apparatus can send the communication permission signal to the wireless in-vivo information acquiring apparatus in order to acquire the in-vivo information, when the communication status between the wireless in-vivo information acquiring apparatus and the communication apparatus is good based on the communication confirmation signal. In addition, the communication apparatus acquires in-vivo information as, for example, plural frames of images while the communication status is good. Therefore, the communication apparatus loses less images. Thus, more accurate in-vivo information can be acquired.

In the communication apparatus, the communication permission signal may also serve as a radio signal for supplying power to the wireless in-vivo information acquiring apparatus. In the communication apparatus, one signal can be employed both as the radio signal for power supply and the communication permission signal, whereby a single transmitting unit can supply power and transmit the communication permission signal at the same time. Thus, the structure of the communication apparatus can be simplified and the communication apparatus as a whole can be downsized.

In the communication apparatus, the communication permission signal transmitting unit may transmit the communication permission signal at a longer interval than an interval of transmission of the communication confirmation signals from the wireless in-vivo information acquiring apparatus, while the communication confirmation signal is not received. In the communication apparatus according, the communication permission signals, which also serve as the power supply signals, are transmitted at longer intervals than the interval of the transmission of the communication confirmation signals, and the power is supplied to the wireless in-vivo information acquiring apparatus at appropriate time. Therefore, the wireless in-vivo information acquiring apparatus does not become unable to transmit the communication confirmation signals due to battery exhaustion. Thus, the in-vivo information can be surely acquired.

Effect of the Invention

According to the present invention, the wireless in-vivo information acquiring apparatus and the wireless in-vivo information acquiring system take in the control signals sequentially sent from the communication apparatus outside the subject by the radio receiving unit, and control the activation of the function executing unit according to the discontinuous state of the inputs of the control signals. Therefore, the wireless in-vivo information acquiring apparatus can be started to be driven at a previously set given time. Thus, the collection and the transmission of the images inside the subject can be accurately performed.

Further, according to the present invention, the activating signals sent from the communication apparatus outside the subject are taken in via the radio receiving unit, and the activation of the function executing unit is controlled according to the inputs of the activating signals. Therefore, the wireless in-vivo information acquiring apparatus can be started to be driven at a previously set given time. Thus, the collection and the transmission of the images inside the subject can be accurately performed.

Still further, according to the present invention, power is supplied to the acquiring unit such as an imaging device and the radio transmitting unit such as a radio transmitter for activation, after a predetermined time elapses since the input of the activating signal. Therefore, the wireless in-vivo information acquiring apparatus can be started to be driven at a previously set given time. Thus, useless image signals are not acquired and power consumption can be reduced. Further, the collection and the transmission of the images inside the subject can be accurately performed.

Still further, according to the present invention, the transmission and the reception of the in-vivo information are performed when the communication status between the wireless in-vivo information acquiring apparatus and the communication apparatus is good. In addition, when the communication status is not good, i.e., when the communication apparatus is unable to receive the in-vivo information, the wireless in-vivo information acquiring apparatus does not transmit images in vain to waste power. In addition, when the communication status is good, the in-vivo information such as plural frames of images are sent. Therefore, the communication apparatus loses less images, and receives the in-vivo information efficiently. Thus, more accurate in-vivo information can be acquired.

BRIEF DESCRIPTION OF DRAWINGS

FIG. 15 is a sectional view of a seventh embodiment of the capsule endoscope according to the present invention;

FIG. 17 is a sectional diagram of an eighth embodiment of the capsule endoscope according to the present invention; and FIG. 18 is a block diagram of the capsule endoscope shown in FIG. 17.

EXPLANATIONS OF LETTERS OR NUMERALS

Figure 1:
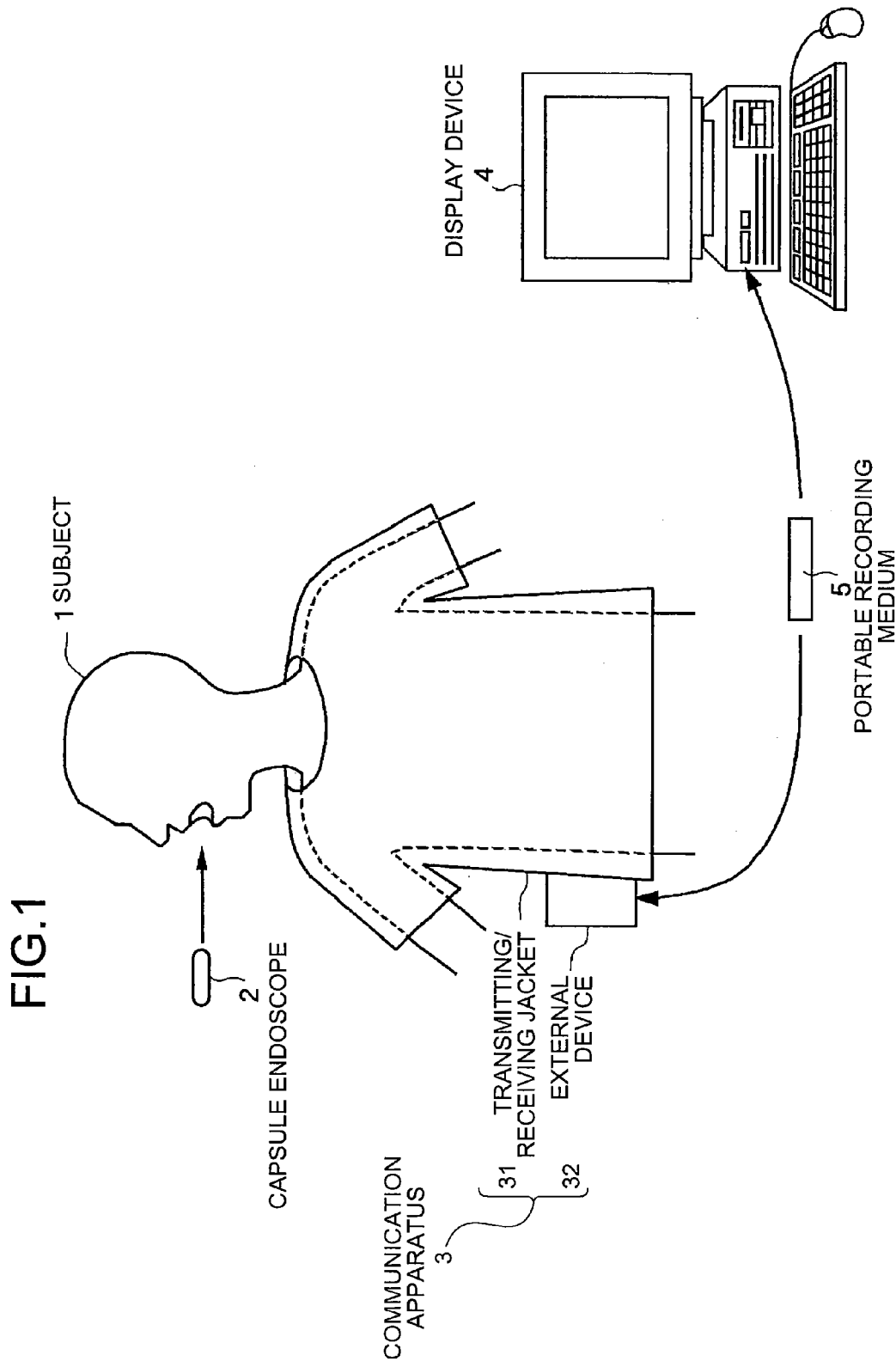
FIG. 1 is a schematic diagram illustrating a concept of a wireless in-vivo information acquiring system according to the present invention.

1, A subject
2, 12, 150, 160 capsule endoscope
3, 13 communication apparatus
4 display device
5 portable recording medium
11 in-vivo information acquiring system
14 workstation
20, 117 light emitting object (LED)
21 LED driving circuit
22 CCD
23 CCD driving circuit
24, 37 RF transmitting unit
25 transmitting antenna unit
26 system control circuit
27 receiving antenna unit
27a coil
27b diode
27c, 28b condenser
28 control-signal detecting circuit
28a control-signal output unit
28c resistor 29 battery
31 transmitting/receiving jacket
32, 130 external device
33 RF receiving unit
34 image processing unit
35 storage unit
36 control-signal input unit
38 power supply unit
40 intra-capsule function executing circuit
41 power supply IC
42 separating circuit
43 power reproducing circuit
44 booster circuit
45 capacitor
50 oscillator
51 superimposing circuit
110 acquiring unit
111 transmitting unit
112 receiving unit
113 communication control unit
114 outer casing
115 casing
116 transparent cover
118 objective lens
119 solid-state imaging sensor
120 memory
121 imaging unit control unit
122 modulator
123 demodulator
124 signal processing circuit
125 antenna
126 switch
127 battery
128 power supply circuit
132 receiving antenna unit
133, B1 to Bm transmitting antenna
135 receiving unit
136 recording unit
137 communication-permission-signal generating unit
138 communication permission signal transmitting unit
140 receiving circuit
141 signal processing circuit
142 selective control unit
145 control unit
146 transmitting circuit
147 display unit
151, 161 coil-like antenna
152 received signal detecting circuit (envelope detecting circuit)
155 diode
156 condenser
157 resistor
158 comparator
159 reference voltage generator
162 power receiving unit
163 rectifying circuit
164 communication permission detecting unit
165 capacitor
A1 to An receiving antenna

BEST MODE(S) FOR CARRYING OUT THE INVENTION

Exemplary embodiments of a wireless in-vivo information acquiring apparatus and a wireless in-vivo information acquiring system according to the present invention will be described in detail below with reference to FIGS. 1 to 18. Elements shown in FIG. 1 will be denoted by the same reference characters throughout the drawings for the convenience of description. It should be noted that the present invention is not limited to the embodiments and various modification can be made to the embodiments without departing from the scope of the present invention.

First Embodiment

FIG. 1 is a conceptual diagram illustrating a concept of the wireless in-vivo information acquiring system according to the present invention. In FIG. 1, a capsule endoscope system includes a swallowable capsule endoscope 2 and a communication apparatus 3. The swallowable capsule endoscope 2 is introduced inside body cavities of a subject 1 and serves as the wireless in-vivo information acquiring apparatus. The communication apparatus 3 is arranged outside the subject 1 and serves as an extracorporeal device that performs radio communication of various types of information with the capsule endoscope 2. Further, the wireless in-vivo information acquiring system includes a display device 4 and a portable recording medium 5. The display device 4 displays an image based on data received by the communication apparatus 3. The portable recording medium 5 performs data transfer between the communication apparatus 3 and the display device 4.

Figure 2:
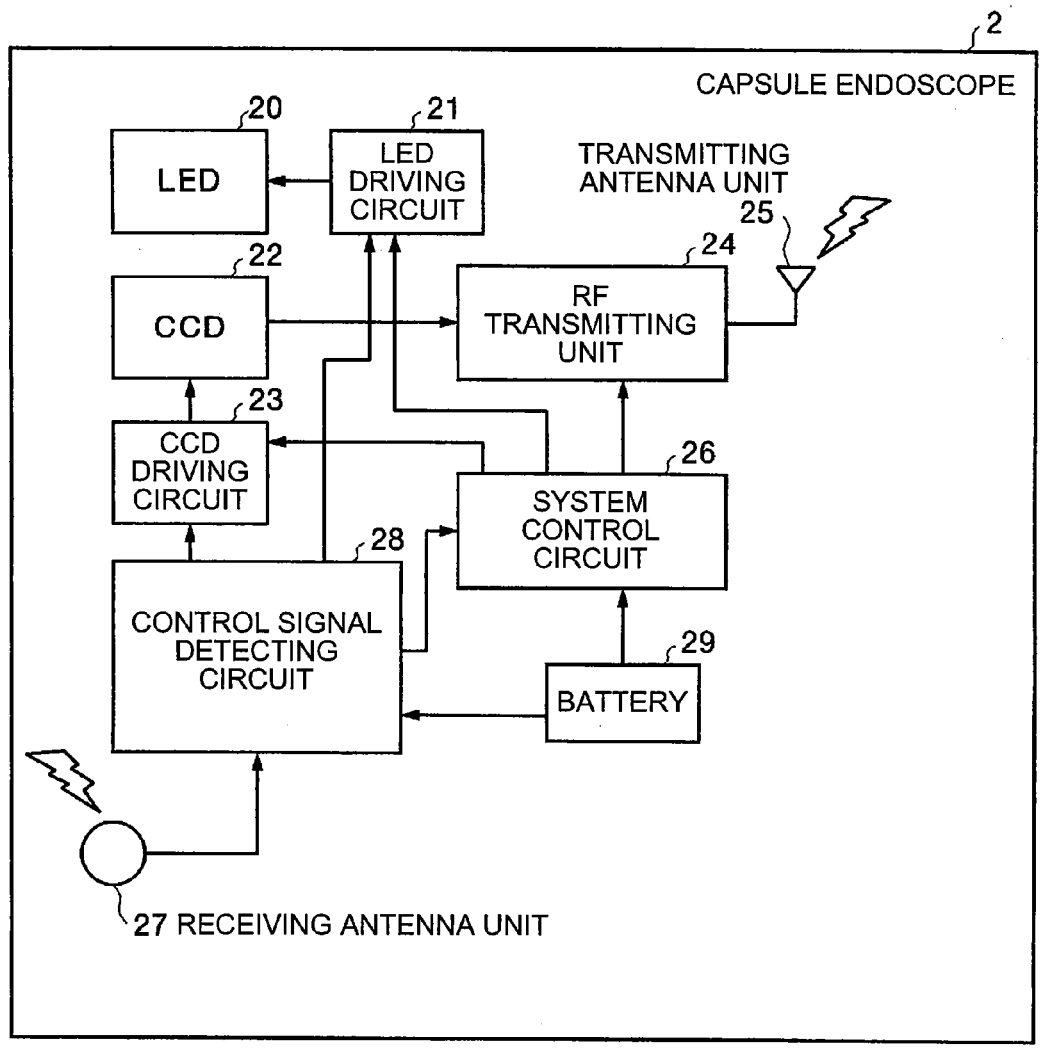
FIG. 2 is a block diagram of an internal structure of a first embodiment of a capsule endoscope shown in FIG. 1.

The capsule endoscope 2 includes for example, as shown in a block diagram of FIG. 2, a light emitting element (LED) 20, an LED driving circuit 21, a charge coupled device (CCD) 22, a CCD driving circuit 23, an RF transmitting unit 24, and a transmitting antenna unit 25. The LED 20 serves as an illuminating unit for illuminating an examined region inside the body cavity of the subject 1. The LED driving circuit 21 controls a driven state of the LED 20. The CCD 22 serves as a function executing unit (acquiring unit) that picks up images inside the body cavity (in-vivo information) by receiving a reflective light from a region illuminated by the LED 20. The CCD driving circuit 23 controls a driven state of the CCD 22. The RF transmitting unit 24 modulates image signals acquired by image pick-up into RF signals. The transmitting antenna unit 25 serves as a function executing unit (radio transmitting unit) that radio transmits the RF signals output from the RF transmitting unit 24. The capsule endoscope 2 further includes a system control circuit 26 which controls operations of the LED driving circuit 21, the CCD driving circuit 23, and the RF transmitting unit 24. Thus, the capsule endoscope 2 operates so as to acquire image data of the examined region illuminated by the LED 20 using the CCD 22 while traveling inside the subject 1. The acquired image data is converted into RF signals by the RF transmitting unit 24, and the RF signals are transmitted via the transmitting antenna unit 25 to the outside of the subject 1.

The capsule endoscope 2 further includes a receiving antenna unit 27, a control-signal detecting circuit 28, and a battery 29. The receiving antenna unit 27 serves as a radio receiving unit that can receive radio signals sequentially transmitted from the communication apparatus 3. The control-signal detecting circuit 28 detects discontinuation in input of signals received by the receiving antenna unit 27 (for example, the control-signal detecting circuit 28 determines there is discontinuation when the intensity of a received signal is equal to or lower than a predetermined level). The battery 29 serves to supply power to the system control circuit 26 and the control-signal detecting circuit 28.

When the control-signal detecting circuit 28 detects that the intensities of sequentially received signals become equal to or lower than a predetermined level, in other words, when the capsule endoscope 2 is introduced inside the subject 1 which serves to attenuate the signals and lower the intensity of the received signal to a level equal to or lower than the predetermined level, the control-signal detecting circuit 28 determines that there is discontinuation in input of the received signals, and supplies a control signal to the system control circuit 26. The system control circuit 26 has a function of distributing driving power supplied from the battery 29 to other elements (function executing units) according to the control signal. After determining that there is discontinuation in the received signals, the control-signal detecting circuit 28 can detect a content of a control signal received by the receiving antenna unit 27 to supply control signals to the LED driving circuit 21, the CCD driving circuit 23, and the system control circuit 26 as necessary.

The system control circuit 26 includes a switch element, a latch circuit (not shown), and the like. These elements are connected between the battery 29 and each element and function to switch over the connection, for example. On receiving a control signal supplied from the control-signal detecting circuit 28 as described above, the latch circuit turns the switch element into an ON-state. Thereafter, the latch circuit maintains the ON-state of the switch element to supply the driving power from the battery 29 to each element of the capsule endoscope 2. In the first embodiment, elements that are provided in the capsule endoscope 2 and have (a part of) the imaging function, illuminating function, and radio function are generically referred to as the function executing units. Specifically, the elements other than the system control circuit 26, the receiving antenna unit 27, and the control-signal detecting circuit 28 are function executing units that execute a predetermined function. The function executing units are collectively referred to as an intra-capsule function executing circuit below as necessary.

Figure 3:
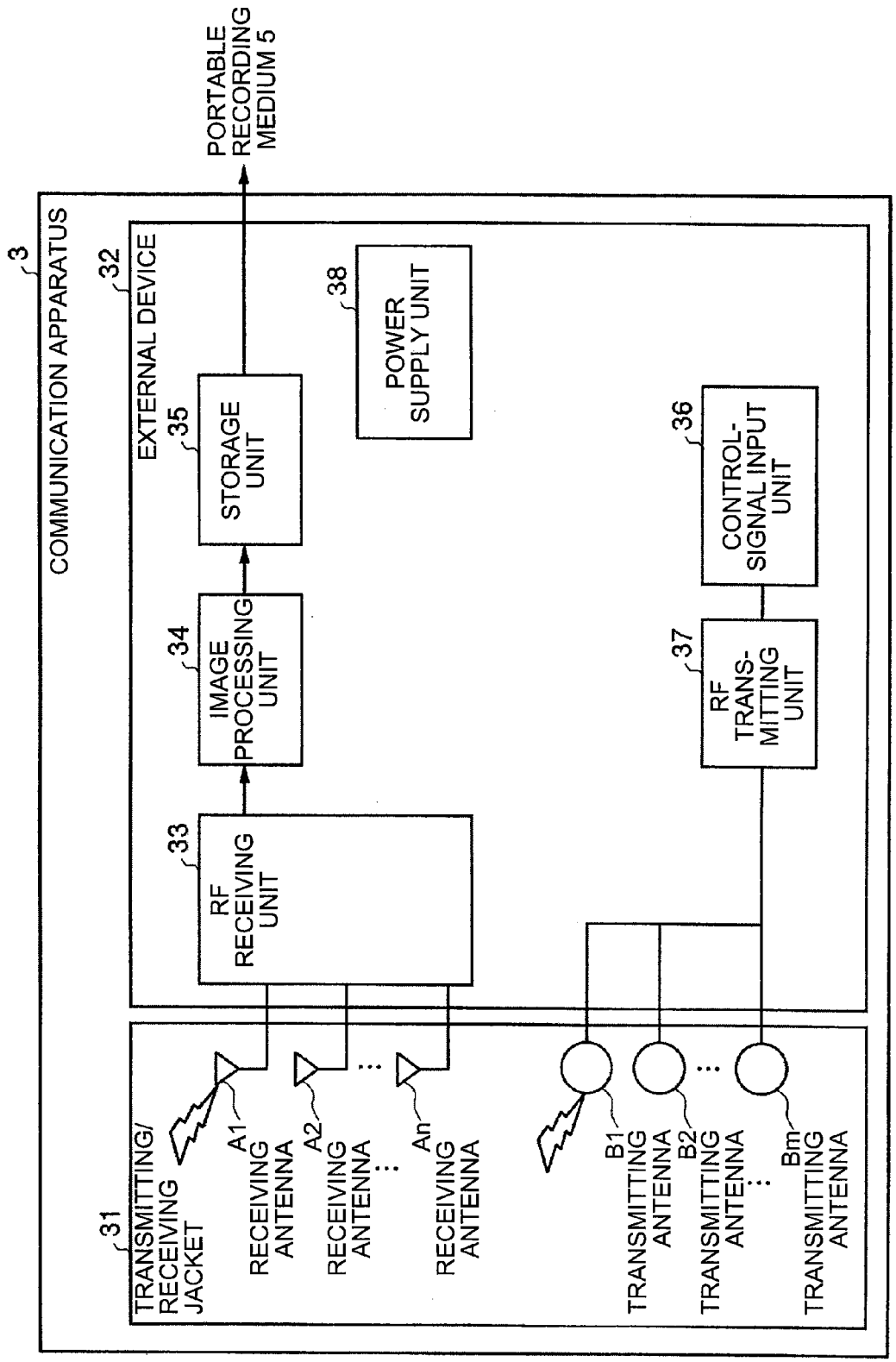
FIG. 3 is a block diagram of an internal structure of the first embodiment of a communication apparatus shown in FIG. 1.

The communication apparatus 3 has a function of a transmitting device and serves as a radio transmitting unit that transmits control signals to the capsule endoscope 2. At the same time, the communication apparatus 3 has a function of a communication device and serves as a radio receiving unit that receives image data captured inside the body cavities and radio transmitted from the capsule endoscope 2. FIG. 3 is a block diagram of an internal structure of the communication apparatus 3 according to the first embodiment shown in FIG. 1. In FIG. 3, the communication apparatus 3 includes a transmitting/receiving garment (jacket that can perform transmission and reception, for example) 31 and an external device 32. The subject 1 wears the jacket 31. The jacket 31 is provided with plural receiving antennas A1 to An and plural transmitting antennas B1 to Bm. The external device 32 performs signal processing of the received/transmitted radio signals. Here, the characters n and m indicate numbers of antennas, and are set to any numbers as necessary.

The external device 32 includes an RF receiving unit 33, an image processing unit 34, and a storage unit 35. The RF receiving unit 33 performs predetermined signal processing such as demodulation on the radio signals received by the receiving antennas A1 to An, and extracts image data acquired by the capsule endoscope 2 from the radio signals. The image processing unit 34 performs a necessary image processing on the extracted image data. The image data after the image processing is stored in the storage unit 35. Thus, the external device 32 performs signal processing on the radio signals transmitted from the capsule endoscope 2. In the embodiment, the image data is stored in the portable recording medium 5 via the storage unit 35.

The external device 32 further includes a control-signal input unit 36 and an RF transmitting unit 37. The control-signal input unit 36 generates a control signal to control a driven state of the capsule endoscope 2. The RF transmitting unit 37 converts a frequency of the generated control signal into radio frequency and outputs the result. The signal acquired after conversion in the RF transmitting unit 37 is supplied to the transmitting antennas B1 to Bm and transmitted to the capsule endoscope 2. The external device 32 generates and outputs the control signal to the transmitting antennas B1 to Bm even while the capsule endoscope 2 is in a standby state prior to the introduction into the subject 1. Further, the external device 32 includes a power supply unit 38 which is provided with a predetermined capacitor or an AC power adaptor. Each element in the external device 32 uses the power supplied from the power supply unit 38 as driving energy.

The control signal may be attenuated by the presence of the subject 1 while being transmitted to the capsule endoscope 2 inside the subject 1. In view of such possible attenuation, the control-signal input unit 36 generates the control signal by adjusting the intensity of the signal to be transmitted, so that the intensity of the signal received by the capsule endoscope 2 is equal to or lower than a predetermined level. The control signals thus generated are sequentially transmitted via the transmitting antennas B1 to Bm to the capsule endoscope 2.

The display device 4 serves to display images that are picked up by the capsule endoscope 2 inside the body cavities. The display device 4 has a configuration like a workstation that displays images based on data retrieved from the portable recording medium 5. Specifically, the display device 4 may directly display images on a CRT display, a liquid crystal display, or the like. Alternatively, the display device 4 may output images to other media as in a printer.

The portable recording medium 5 can be connected to the external device 32 and the display device 4. When the portable recording medium 5 is inserted into and connected to one of the external device 32 and the display device 4, information can be retrieved from or recorded into the portable recording medium 5. In the embodiment, while the capsule endoscope 2 is traveling inside the body cavities of the subject 1, the portable recording medium 5 is inserted into the external device 32 and records data transmitted from the capsule endoscope 2. After the capsule endoscope 2 is discharged from the subject 1, i.e., after the imaging inside the subject 1 is finished, the portable recording medium 5 is removed from the external device 32 and inserted into the display device 4. Then, the display device 4 reads out the data recorded in the portable recording medium 5. The portable recording medium 5 includes, for example, Compact Flash (registered trademark) memory. The portable recording medium 5 can indirectly transfer data between the external device 32 and the display device 4. Therefore, dissimilar to a system in which the external device 32 and the display device 4 are directly connected by a cable, the subject 1 can freely move during the imaging inside the body cavities.

Figure 4:
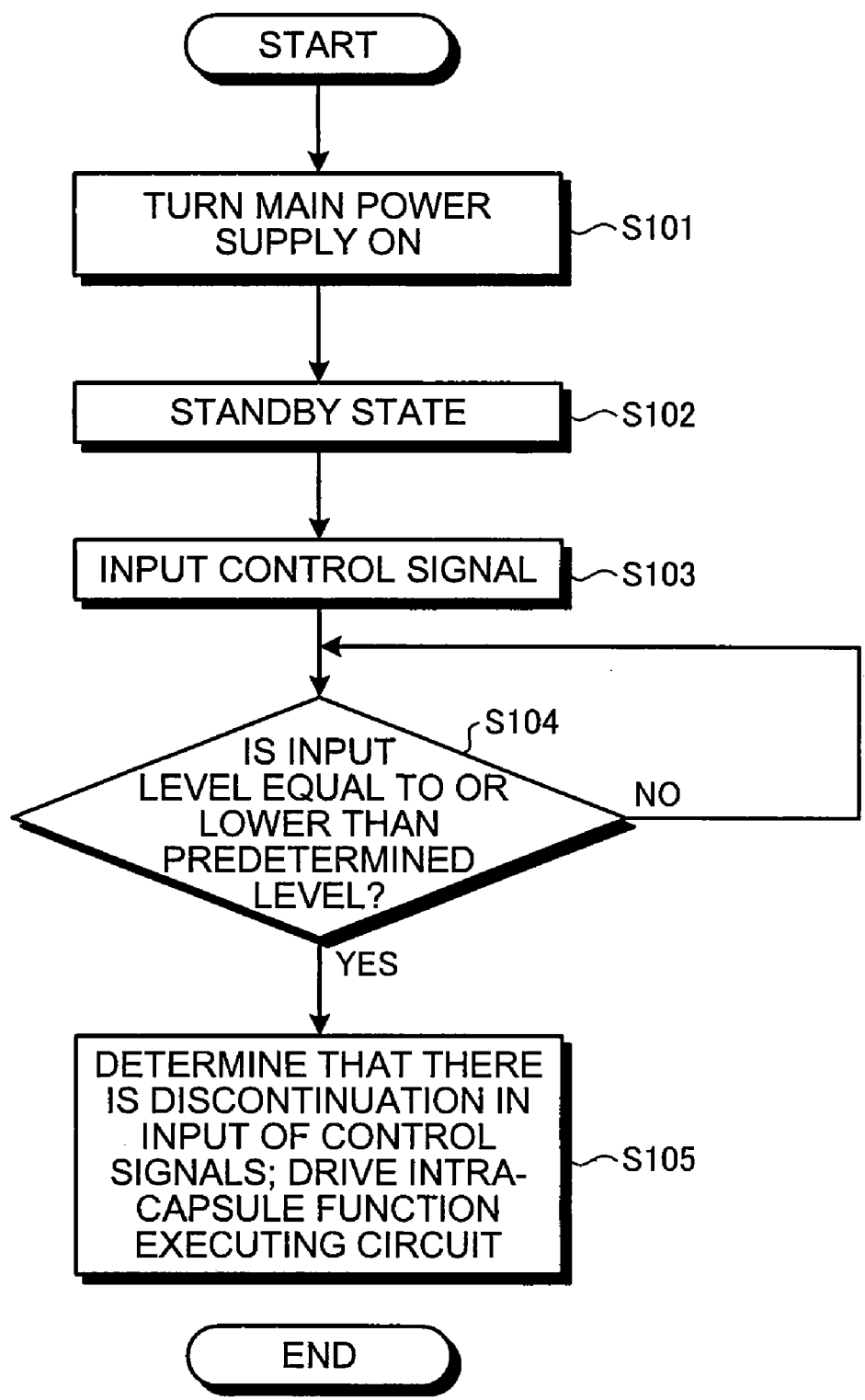
FIG. 4 is a flowchart of an operation of the capsule endoscope.

An operation of the capsule endoscope 2 will be described with reference to a flowchart of FIG. 4. In FIG. 4, the capsule endoscope 2 prior to the introduction into the subject 1, for example, incorporates a lead switch (not shown) that is turned on and off in response to presence/absence of an external magnetic field. While being in storage, the capsule endoscope 2 is housed inside a package together with a permanent magnet that supplies the external magnetic field. In this state, the capsule endoscope 2 cannot be driven.

Before being swallowed, the capsule endoscope 2 is taken out of the package. Then, the capsule endoscope is separated from the permanent magnet in the package, i.e., taken away from an influence of the magnetic field. Thus, a main power supply of the capsule endoscope 2 is turned on (step S101) and the capsule endoscope 2 is turned into a standby state (step S102). While the capsule endoscope 2 is in the standby state, the battery 29 supplies power to the system control circuit 26 and the control-signal detecting circuit 28 as shown in FIG. 2, whereby the receiving antenna unit 27 is made capable of receiving the radio signals. Here, power is not supplied to other function executing circuits.

When the capsule endoscope 2 is in the standby state, the communication apparatus 3 sequentially transmits the control signals to the capsule endoscope 2. The capsule endoscope 2 receives the control signals by the receiving antenna unit 27 (step S103), and the control-signal detecting circuit 28 checks if the input level (level of intensity) of the received control signal is equal to or lower than the predetermined level (step S104)

Before the capsule endoscope 2 is introduced inside the subject 1, the intensity level of the control signal received by the capsule endoscope 2 is higher than the predetermined level, whereas after the capsule endoscope 2 is introduced inside the subject 1, the control signal transmitted from the communication apparatus 3 is attenuated by the subject 1, and the intensity level of the control signal received by the capsule endoscope 2 becomes equal to or lower than the predetermined level. On detecting the control signal with an intensity level equal to or lower than the predetermined level, the control-signal detecting circuit 28 of the capsule endoscope 2 determines that the capsule endoscope 2 is introduced into the subject 1 causing a discontinuous state in signal input. Then, the control-signal detecting circuit 28 supplies a control signal to the system control circuit 26. On receiving the control signal, the system control circuit 26 supplies driving power of the battery to the intra-capsule function executing circuits (i.e., LED driving circuit 21, CCD driving circuit 23, and RF transmitting unit 24 in the embodiment), to control the driving of the intra-capsule function executing circuits (step S105).

When the intra-capsule function executing circuits receive the driving power, the LED driving circuit 21, the CCD driving circuit 23, and the RF transmitting unit 24 are turned on to become active. Further, the reception of the driving power allows the LED 20 to illuminate inside the subject 1 with the illuminating light, the CCD 22 to receive the reflected light of the illuminating light thereby acquiring image data, and the RF transmitting unit 24 to transmit the image data via the transmitting antenna unit 25 to the communication apparatus 3 outside the subject 1.

As can be seen from the foregoing, in the first embodiment, the capsule endoscope detects the discontinuation of the input of the control signals sequentially transmitted from the communication apparatus after the capsule endoscope is introduced into the subject. The driving power is supplied to the intra-capsule function executing circuits based on the result of detection for the driving control of the intra-capsule function executing circuits. Therefore, a time to start driving the capsule endoscope can be set to a time after the capsule endoscope is securely placed inside the subject, whereby the image can be collected and transmitted appropriately inside the subject.

In the wireless intra subject information acquiring system according to the first embodiment described above, if the system detects the discontinuation in the input of the control signals at the moment the capsule endoscope is placed inside the mouth of the subject, the intra-capsule function executing circuit may be driven immediately after the introduction of the capsule endoscope into the mouth. In some cases, however, it is desirable to drive the intra-capsule function executing circuit after the capsule endoscope 2 is surely placed inside an organ to be examined, rather than right after the capsule endoscope 2 is swallowed by the subject 1.

To meet such a requirement, it may be possible to provide the control-signal detecting circuit 28 with a timer function. Then, the control-signal detecting circuit 28 may be set so that the control-signal detecting circuit 28 supplies a control signal to the system control circuit 26 after a predetermined time period passes since the detection of the discontinuation in the input of the control signal. In response to the control signal, driving power may be supplied to the intra-capsule function executing circuits after the predetermined time period passes, so that the imaging of the examined region and the collection and the transmission of the image data are allowed.

When the collection and the transmission of the image data are to be performed after the capsule endoscope 2 reaches inside the stomach, time required for the capsule endoscope 2 to reach the stomach may be set in the timer as a predetermined standby time after the detection of discontinuation in the input of the control signals. On detecting the discontinuation in the input of the control signals, the control-signal detecting circuit 28 activates the timer. After the set time elapses, the control-signal detecting circuit 28 supplies a control signal to the system control circuit 26 to turn the switch element of the system control circuit 26 to an ON-state. Accordingly, the driving power is supplied to the intra-capsule function executing circuits from the battery 29 after the capsule endoscope is surely placed inside the stomach, i.e., the organ to be examined, whereby image data of an interior of the stomach which is illuminated by the LED 20 is acquired through imaging by the CCD 22, and externally transmitted.

In the first embodiment, the driving power is supplied to the intra-capsule function executing circuits at the moment the capsule endoscope is introduced inside the object of examination. Therefore, the power consumption can be reduced. Further, the driving can be started at any time as previously set. Therefore, the collection and the transmission of the image of the object of examination can be performed appropriately inside the subject.

Further, in the first embodiment, the system control circuit 26 has a latch circuit. Therefore, after the intra-capsule function executing circuits start to be driven in step S105, the intra-capsule function executing circuits keep being driven regardless of the presence/absence of the control signal input. The driving of the intra-capsule function executing circuits may be stopped based on a function of another timer provided in the system control circuit 26, for example.

Further, in the first embodiment, once the capsule endoscope 2 determines that there is a discontinuation in the input of the control signals for the drive control, the capsule endoscope 2 does not need to take in the control signals. However, the communication apparatus 3 keeps on sequentially transmitting the control signals. The transmission of the control signals may be stopped based on a function of a timer provided in the control-signal input unit 36, for example, so that the transmission halts in a predetermined time period after the transmission starts (for example, after a time required for the capsule endoscope 2 to be securely placed inside the subject 1 has passed). Alternatively, the transmission of the control signals may be stopped when the communication apparatus 3 receives the image data from the capsule endoscope 2.

Further, in the first embodiment, the control-signal input unit 36 of the external device 32 can generate various types of control signals for controlling the function of the function executing circuits inside the capsule endoscope 2, and the control-signal detecting circuit 28 of the capsule endoscope 2 can detect the generated control signals and control each of the function executing circuits inside the capsule endoscope 2 according to the detected control signal. Here, it is necessary to set the control signals so that the intensity of the received control signals is easily detectable by the capsule endoscope 2 inside the subject 1.

Second Embodiment

Figure 5:
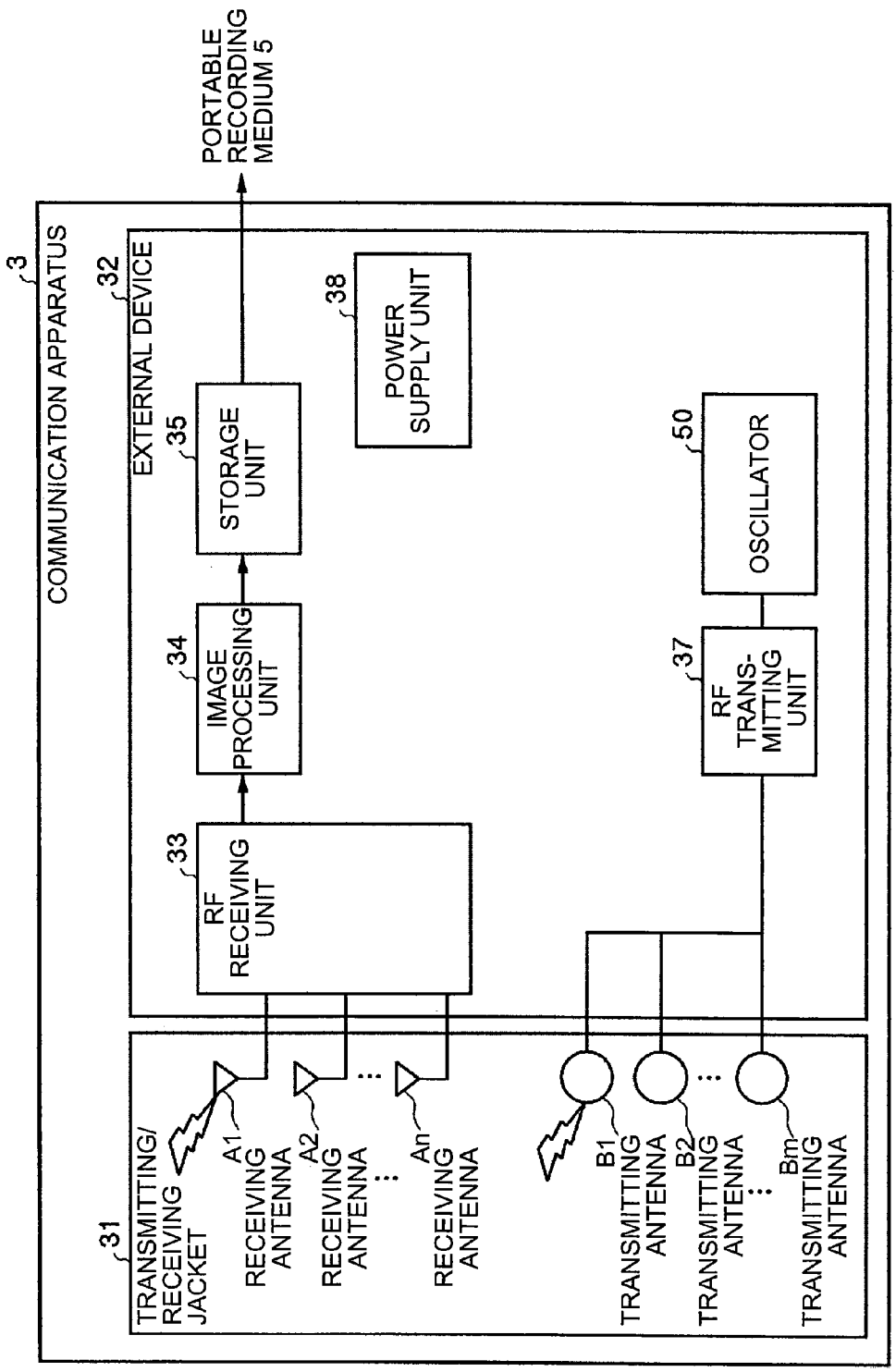
FIG. 5 is a block diagram of a second embodiment of the internal structure of the communication apparatus shown in FIG. 1.

FIG. 5 is a block diagram of an internal structure of a communication apparatus according to a second embodiment. The communication apparatus 3 according to the second embodiment is different from the communication apparatus 3 of the first embodiment in that an oscillator 50 that regulates an oscillating frequency of the control signal is connected to the RF transmitting unit 37 as shown in FIG. 5 instead of the control-signal input unit 36 of the communication apparatus shown in FIG. 3. Since the structure of the capsule endoscope 2 in the second embodiment is similar to the structure shown in FIG. 2, the description thereof will not be repeated. The control-signal detecting circuit 28 in the second embodiment, however, includes a narrow band filter that detects control signals of a predetermined frequency band. Further, the frequency of the control signal is preferably set in a frequency band which is different from a frequency band of normal radio signals.

In the second embodiment with the above described structure, when the capsule endoscope 2 becomes unable to detect the input of the control signals that are sequentially oscillated from the communication apparatus 2 and in the predetermined frequency band, the control-signal detecting circuit 28 determines that the capsule endoscope 2 has been placed inside the subject 1, and the system control circuit 26 supplies power to the intra-capsule function executing circuits to turn the intra-capsule function executing circuits into an active state, i.e., a state in which the circuits can be activated.

As can be seen from the foregoing, in the second embodiment, when the capsule endoscope is introduced into the subject, the input of the control signals that are externally transmitted and that have the predetermined frequency band becomes discontinuous. Based on the detection of the discontinuation in the input, the power is supplied to the intra-capsule function executing circuits and the driving of the intra-capsule function executing circuits is controlled. Therefore, the time to start driving the capsule endoscope can be set to a time after the capsule endoscope is securely placed inside the subject. Further, the control signals to be transmitted and received are within a narrow band. Therefore, the transmission is not affected by noise, and the collection and the transmission of images inside the subject can be performed appropriately.

In the second embodiment, a timer function as the first embodiment may be provided, so that the power is supplied to the intra-capsule function executing circuits after the capsule endoscope is securely placed inside the organ to be examined.

Third Embodiment

Similar to the embodiments described above, a wireless in-vivo information acquiring system according to a third embodiment includes, as shown in FIG. 1, the swallowable capsule endoscope 2 which is introduced inside the body cavities of the subject 1 and serves as a wireless in-vivo information acquiring apparatus, and the communication apparatus 3 which is arranged outside the subject 1 and serves as an extracorporeal device that performs radio communication of various types of information with the capsule endoscope 2. Further, the wireless in-vivo information acquiring system includes the display device 4 that displays images based on data received by the communication apparatus 3 and the portable recording medium 5 that transfers data between the communication apparatus 3 and the display device 4.

A block structure of the capsule endoscope 2 includes, similar to that shown in FIG. 2, the light emitting element (LED) 20 that serves as an illuminating unit that illuminates an examined region inside the body cavity of the subject 1, the LED driving circuit 21 that controls a driven state of the LED 20, the charge coupled device (CCD) 22 that serves as a function executing unit (acquiring unit) that picks up an image inside the body cavity (in-vivo information) by receiving a reflected light from the region illuminated by the LED 20, the CCD driving circuit 23 that controls a driven state of the CCD 22, the RF transmitting unit 24 that modulates image signals acquired by image pick-up into RF signals, and the transmitting antenna unit 25 that serves as a function executing unit (radio transmitting unit) that transmits the RF signals output from the RF transmitting unit 24 by radio. The capsule endoscope 2 further includes the system control circuit 26 that controls the operations of the LED driving circuit 21, the CCD driving circuit 23, and the RF transmitting unit 24, whereby the capsule endoscope 2 works so as to acquire image data of the examined region illuminated by the LED 20 using the CCD 22 while being placed inside the subject 1. The acquired image data is converted into the RF signals by the RF transmitting unit 24 and transmitted outside the subject 1 by the transmitting antenna unit 25.

The capsule endoscope 2 further includes the receiving antenna unit 27 which serves as a radio receiving unit that can receive the radio signals transmitted from the communication apparatus 3, the control-signal detecting circuit 28 which detects a control signal of a predetermined input level (reception intensity level, for example) among the signals received by the receiving antenna unit 27, and the battery 29 that supplies power to the system control circuit 26 and the control-signal detecting circuit 28.

The control-signal detecting circuit 28 detects a signal whose input level is equal to or higher than a predetermined input level (activating signal) from the received signals. On the one hand, the control-signal detecting circuit 28 supplies the activating signals to the system control circuit 26. On the other hand, the control-signal detecting circuit 28 detects a content of the control signal and outputs control signals to the LED driving circuit 21, the CCD driving circuit 23, and the system control circuit 26 as necessary. The system control circuit 26 has a function of distributing the driving power supplied from the battery 29 to the other elements (function executing units).

The system control circuit 26 includes a switch element, a latch circuit (not shown), and the like. These elements are connected between each element and the battery 29 and have a function of switching over the connection, for example. On receiving the control signal (activating signal) from the control-signal detecting circuit 28, the latch circuit turns the switch element to an ON-state, and subsequently maintains the ON-state of the switch element to supply the driving power to each element inside the capsule endoscope 2. In the third embodiment, the elements having (a part of) functions of imaging, illuminating and radio communication and provided in the capsule endoscope 2 are generically referred to as function executing units that execute a predetermined function. Specifically, the elements other than the system control circuit 26, the receiving antenna unit 27, and the control-signal detecting circuit 28 are the function executing units that execute predetermined function, and those elements will be collectively referred to as an intra-capsule function executing circuit below if necessary.

Figure 6:
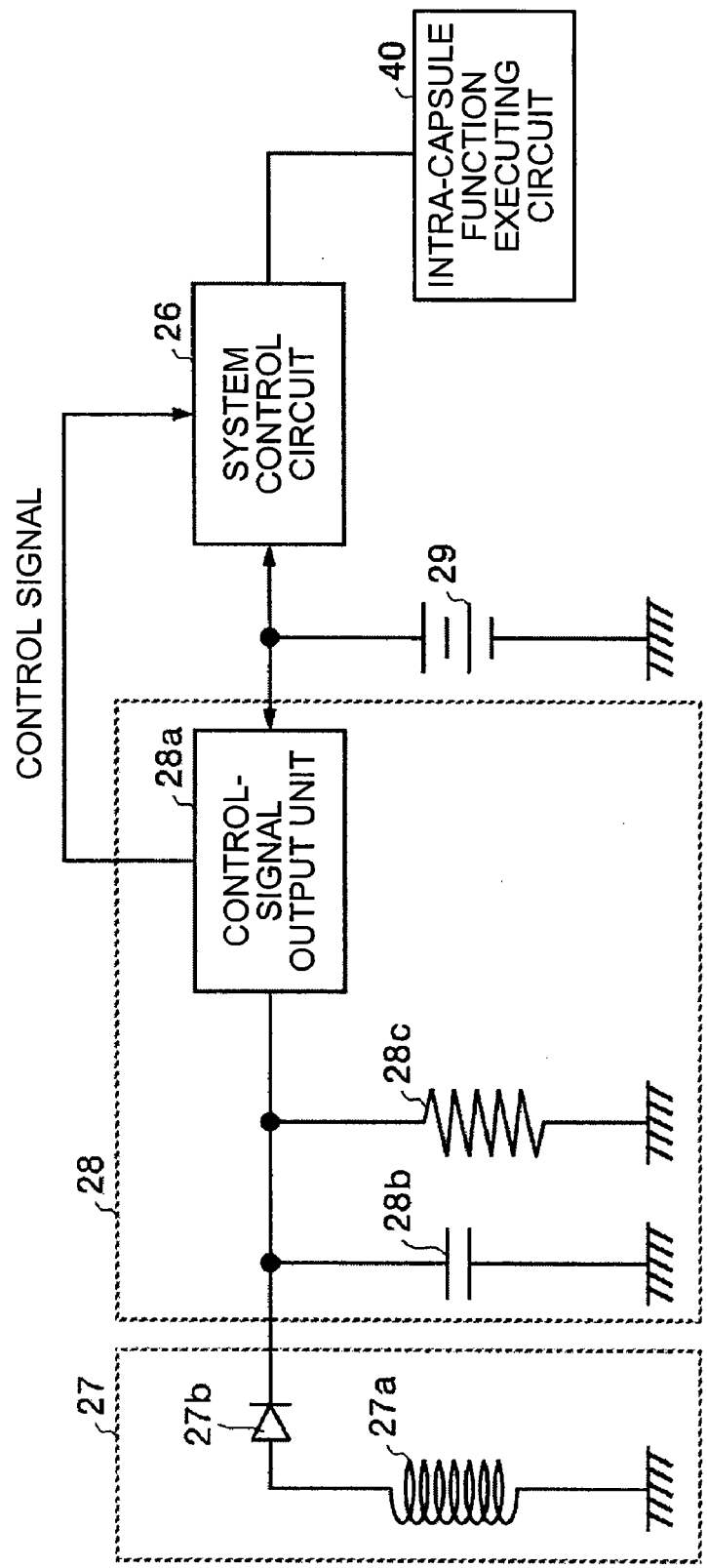
FIG. 6 is a circuit diagram illustrating a circuit structure of a third embodiment of the capsule endoscope shown in FIG. 2.

FIG. 6 is a circuit diagram showing a circuit structure of the capsule endoscope as shown in FIG. 2 according to the third embodiment. In FIG. 6, the receiving antenna unit 27 includes a coil 27a which receives the activating signal to generate electromotive force, and a diode 27b which rectifies the electromotive force. The control-signal detecting circuit 28 includes a control-signal output unit 28a that outputs control signals, a condenser 28b having one end connected between the diode 27b and the control-signal output unit 28a and another end connected to the ground, and a resister 28c having one end connected between the diode 27b and the control-signal output unit 28a and another end connected to the ground. The control-signal detecting circuit 28 detects a signal (activating signal) whose input level is a predetermined level determined by a time constant of the condenser 28b and the resistor 28c, and supplies the detected signal to the control-signal output unit 28a. The control-signal output unit 28a supplies control signals for controlling the operation of the system control circuit 26 based on the input of the activating signal. The switch element in the system control circuit 26 is turned to the ON-state according to the input of the control signal. Consequently, the intra-capsule function executing circuit 40 receives the power supplied from the battery 29, and is turned to a state in which the intra-capsule function executing circuit 40 can be activated.

The communication apparatus 3 has a function of transmitting device and serves as the radio transmitting unit that transmits the activating signal to the capsule endoscope 2. On the other hand, the communication apparatus 3 has a function of communication device and serves as the radio receiving unit that receives the image data that is captured inside the body cavity and transmitted from the capsule endoscope 2 by radio. In the third embodiment, the internal structure of the communication apparatus 3 is similar to the structure shown in the block diagram of FIG. 3. In FIG. 3, the communication apparatus 3 includes the garment for transmission/reception (transmitting/receiving jacket, for example) 31 having plural receiving antennas A1 to An and plural transmitting antennas B1 to Bm, and the external device 32 that performs, for example, signal processing of the radio signals received/transmitted. Here, the characters n and m indicate the number of antennas, and the number of antennas can be set to any number as necessary.

The external device 32, similar to that in the first embodiment, includes the RF receiving unit 33 that performs predetermined signal processing such as demodulation on the radio signals received via the receiving antennas A1 to An to extract image data acquired by the capsule endoscope 2 from the radio signals, the image processing unit 34 that performs necessary image processing on the extracted image data, and the storage unit 35 that serves to record the image data after the image processing. Thus, the external device 32 performs signal processing on the radio signals transmitted from the capsule endoscope 2. In the third embodiment, the image data is recorded into the portable recording medium 5 via the storage unit 35.

The external device 32 further includes the control-signal input unit 36 that generates a control signal (activating signal) for controlling the driven state of the capsule endoscope 2, and the RF transmitting unit circuit 37 that converts the frequency of the generated control signals into radio frequency and outputs the result. The signals acquired after the conversion by the RF transmitting unit circuit 37 are supplied to the transmitting antenna B1 to Bm and transmitted further to the capsule endoscope 2. The external device 32 further includes the power supply unit 38 which is provided with a predetermined battery or an AC power adopter. Each of the elements in the external device 32 uses the power supplied from the power supply unit 38 as driving energy.

The display unit 4 serves to display images that are captured by the capsule endoscope 2 inside the body cavity. The display unit 4 has a configuration like a workstation that displays images based on the data retrieved from the portable recording medium 5. Specifically, the display device 4 may directly display the images as in a CRT display, a liquid crystal display, or the like. Alternatively, the display device 4 may output the image to other media as in a printer.

The portable recording medium 5 can be connected to the external device 32 and the display device 4. When the portable recording medium 5 is inserted into and connected to one of the external device 32 and the display device 4, information can be retrieved from or recorded into the portable recording medium 5. In the third embodiment, the portable recording medium 5 is inserted into the external device 32 and records data transmitted from the capsule endoscope 2 while the capsule endoscope 2 is traveling through the body cavities of the subject 1. After the capsule endoscope 2 is discharged from the subject 1, i.e., after the capsule endoscope 2 finishes imaging inside the subject 1, the portable recording medium 5 is removed from the external device 32 and inserted into the display device 4. Then, the display device 4 reads out the data recorded in the portable recording medium 5. The portable recording medium 5 includes, for example, a Compact Flash (registered trademark) memory. The portable recording medium 5 can indirectly transfer data between the external device 32 and the display device 4. Therefore, dissimilar to a system in which the external device 32 and the display device 4 are directly connected by a cable, the subject 1 can freely move during the imaging inside the body cavities.

Figure 7:
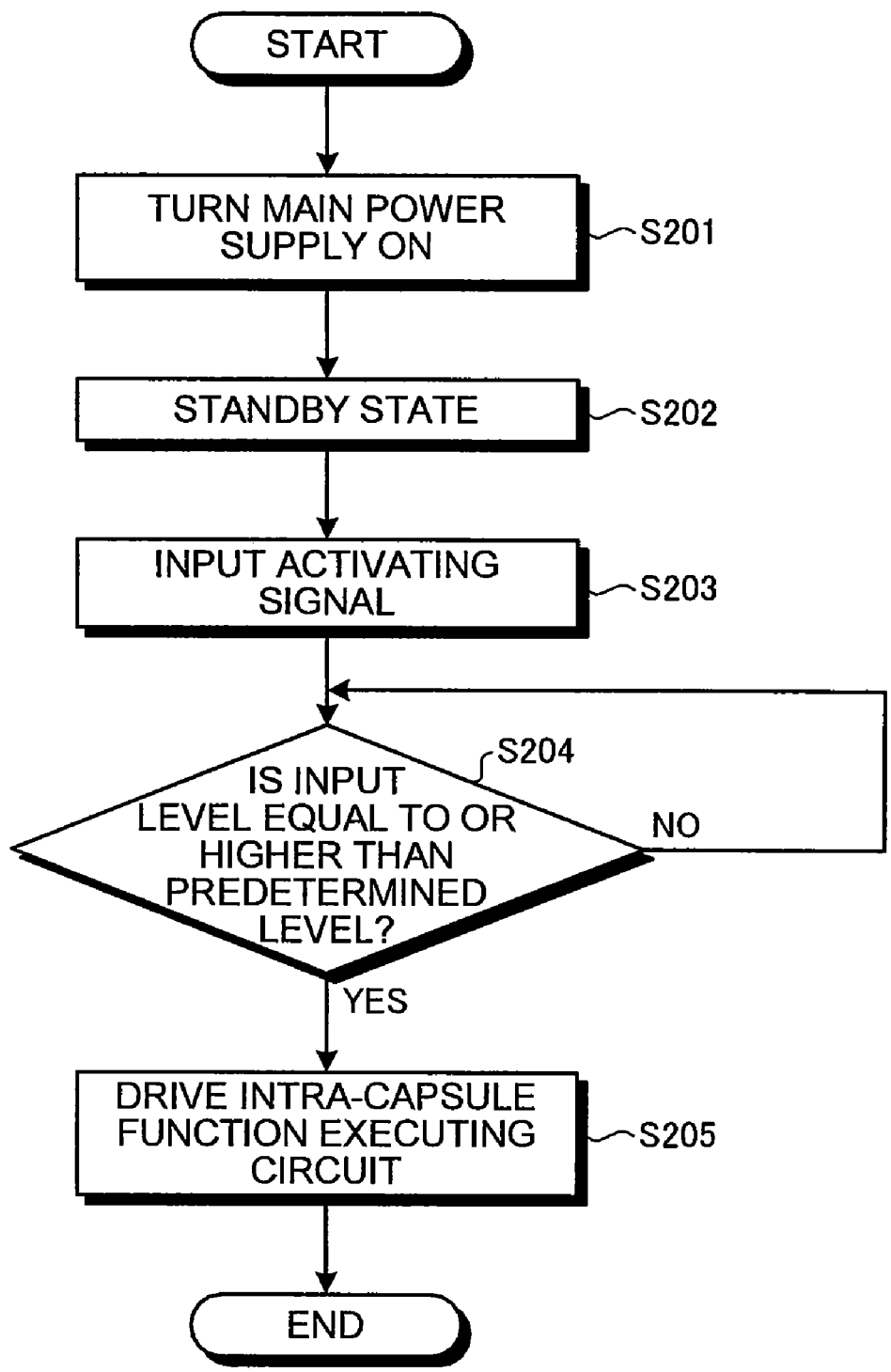
FIG. 7 is a flowchart illustrating an operation of the capsule endoscope.

An operation of the capsule endoscope 2 will be described with reference to a flowchart of FIG. 7. In FIG. 7, prior to the introduction into the subject 1, the capsule endoscope 2 includes a lead switch (not shown) which is turned on and off in response to the presence/absence of an external magnetic field. While being in storage, the capsule endoscope 2 is housed inside a package together with a permanent magnet which supplies the external magnetic field. In this state, the capsule endoscope 2 cannot be driven.

Before being swallowed, the capsule endoscope 2 is taken out of the package. Then, the capsule endoscope is separated from the permanent magnet in the package, i.e., taken away from an influence of the magnetic field. Then, the main power supply of the capsule endoscope is turned on (step 201) and the capsule endoscope is turned into a standby state (step 202). While the capsule endoscope 2 is in the standby state, the battery 29 supplies power to the system control circuit 26 and the control-signal detecting circuit 28 as shown in FIG. 2, whereby the receiving antenna unit 27 is made capable of receiving the radio signals. Here, power is not supplied to other function executing circuits 40.

When the capsule endoscope 2 in the standby state is introduced into the subject 1, the communication apparatus 3 transmits the activating signal to the capsule endoscope 2. Then, the receiving antenna unit 27 of the capsule endoscope 2 receives the activating signals (step 203). When the control-signal detecting circuit 28 detects the activating signal whose input level is equal to or above the predetermined level (step 204), the control-signal detecting circuit 28 outputs the control signal to the system control circuit 26. On taking in the control signal, the system control circuit 26 supplies the driving power of the battery to the intra-capsule function executing circuit 40 (LED driving circuit 21, CCD driving circuit 23, and RF transmitting unit 24 in the third embodiment), thereby controlling the driving of the intra-capsule function executing circuit 40 (step 205).

When the driving power is supplied to the intra-capsule function executing circuit 40, the LED driving circuit 21, the CCD driving circuit 23, and the RF transmitting unit 24 are turned on to become active. Further, the reception of the driving power allows the LED 20 to illuminate inside the subject 1 with the illuminating light, the CCD 22 to receive the reflected light of the illuminating light thereby acquiring image data, and the RF transmitting unit 24 to transmit the image data via the transmitting antenna unit 25 to the communication apparatus 3 outside the subject 1.

As can be seen from the foregoing, in the third embodiment, after being introduced inside the subject, the capsule endoscope inside the subject detects the activating signal which is externally transmitted and whose input level is equal to or above the predetermined level, to supply the driving power to the intra-capsule function executing circuits and to control the driving of the intra-capsule function executing circuits. Therefore, the time to start driving the capsule endoscope can be set to a time after the capsule endoscope is surely placed inside the subject, whereby the collection and the transmission of the image inside the subject can be performed appropriately.

In the wireless in-vivo information acquiring system according to the third embodiment mentioned above, if the activating signal is transmitted at the moment the capsule endoscope is placed in the mouth of the subject, the intra-capsule function executing circuit 40 may start to be driven immediately after the introduction of the capsule endoscope into the mouth. In some cases, however, it is desirable to drive the intra-capsule function executing circuit after the capsule endoscope 2 is surely placed inside the organ to be examined, rather than right after the capsule endoscope 2 is swallowed by the subject 1.

To meet such a requirement, it may be possible to provide the control-signal detecting circuit 28 with a timer function. Then, the control-signal detecting circuit 28 may be set so that the control-signal detecting circuit 28 supplies a control signal to the system control circuit 26 after a predetermined time period passes since the detection of the activating signal. In response to the control signal, driving power may be supplied to the intra-capsule function executing circuits after the predetermined time period passes, so that the imaging of the examined region inside the subject and the collection and the transmission of the image data are allowed.

When the collection and the transmission of the image data are to be performed after the capsule endoscope 2 reaches inside the stomach, time required for the capsule endoscope 2 to reach the stomach may be set in the timer as a predetermined standby time after the transmission of the activating signal. On detecting the activating signal, the control-signal detecting circuit 28 activates the timer. After the set time elapses, the control-signal detecting circuit 28 supplies a control signal to the system control circuit 26 to turn the switch element of the system control circuit 26 to an ON-state. Accordingly, the driving power is supplied to the intra-capsule function executing circuits 40 from the battery 29 after the capsule endoscope is surely placed inside the stomach, i.e., the organ to be examined, whereby image data of an interior of the stomach which is illuminated by the LED 20 is acquired through imaging by the CCD 22, and externally transmitted.

In the third embodiment, the driving power is supplied to the intra-capsule function executing circuits at the moment the capsule endoscope is introduced inside the object of examination. Therefore, the power consumption can be reduced. Further, the driving can be started at any time as previously set. Therefore, the collection and the transmission of the image of the object of examination can be performed appropriately inside the subject.

Further, in the third embodiment, the system control circuit 26 has a latch circuit. Therefore, after the intra-capsule function executing circuits 40 start to be driven in step S105, the intra-capsule function executing circuits 40 keep being driven regardless of the presence/absence of the control signal input. The driving of the intra-capsule function executing circuits 40 may be stopped based on a function of another timer provided in the system control circuit 26, for example.

Further, in the third embodiment, the control-signal input unit 36 of the external device 32 can generate various types of control signals for controlling the function of the function executing circuits 40 inside the capsule endoscope 2, and the control-signal detecting circuit 28 of the capsule endoscope 2 can detect the generated control signals and control each of the function executing circuits inside the capsule endoscope 2 according to the detected control signal.

In the third embodiment, the control-signal input unit 36 may generate a control signal (hereinafter referred to as "activation start command signal") having a predetermined data pattern indicating a command to start the activation after the activating signal. The generated control signal may be transmitted to the capsule endoscope 2. After the control-signal detecting circuit 28 of the capsule endoscope 2 detects the activating signal, the control-signal detecting circuit 28 may detect the activation start command signal based on the data pattern of the received control signal, and supplies the detected activation start command signal to the system control circuit 26.

Thus, when the control signal indicating the command to start activating is transmitted subsequent to the transmission of the activating signal, even if a noise which has substantially the same input level as the input level of the activating signal is generated, and the input level thereof is determined as to satisfy the input level set in step S104 of FIG. 5, the control-signal detecting circuit 28 can determine whether the signal that satisfies the condition of step S104 is a command to drive control the intra-capsule function executing circuit or not based on the data pattern of the control signal transmitted subsequent to the pertinent signal. Thus, the activation start command signal serves to prevent the control-signal detecting circuit 28 from making an erroneous decision under the influence of the noise. Further, the collection and the transmission of the image of the object of examination inside the subject can be performed appropriately.

Fourth Embodiment

Figure 8:
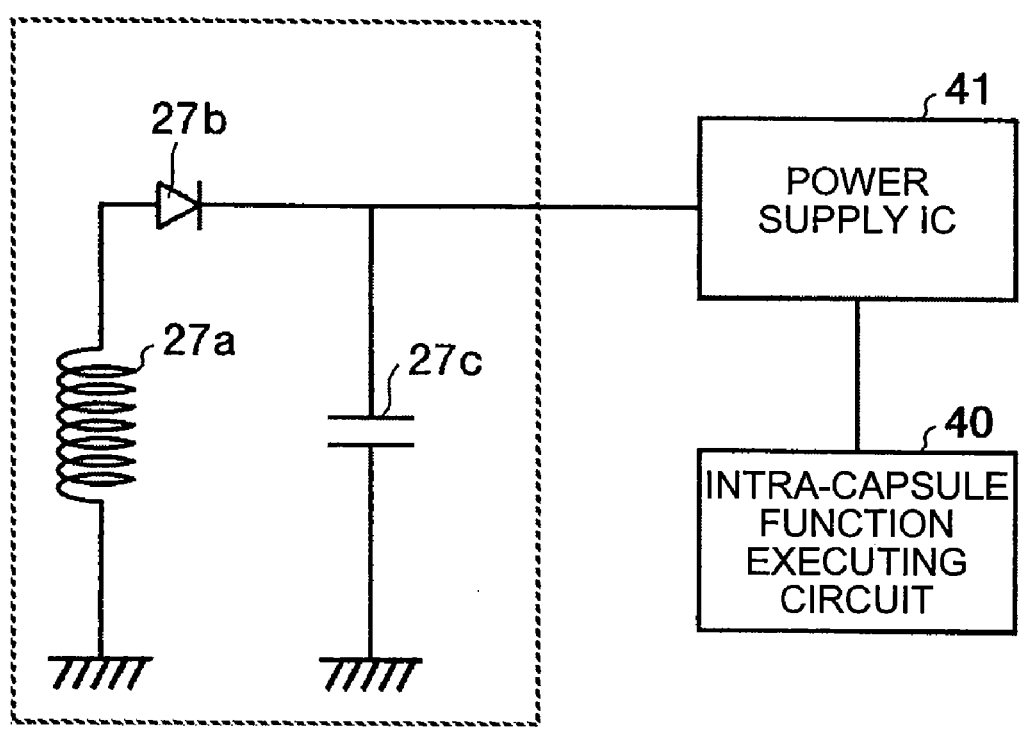
FIG. 8 is a circuit diagram illustrating a circuit structure of a fourth embodiment of the capsule endoscope shown in FIG. 1.

FIG. 8 is a circuit diagram showing a circuit structure of the capsule endoscope as shown in FIG. 1 according to a fourth embodiment. In the fourth embodiment, the capsule endoscope 2 is assumed to have no battery inside. The communication apparatus 3 transmits a power supply signal as an activating signal to the capsule endoscope. The power supply signal serves to supply power to the intra-capsule function executing circuits 40.

In FIG. 8, the capsule endoscope 2 includes the receiving antenna unit 27, a power supply IC 41 including a regulator or a DC-DC converter, and the intra-capsule function executing circuit 40. The receiving antenna unit 27 includes the coil 27a that receives the activating signal to generate electromotive force, the diode 27b that rectifies the electromotive force, and a condenser 27c that has a function of supplying power.

Further, the communication apparatus 3 of the fourth embodiment is different from the communication apparatus shown in FIG. 3 in that the communication apparatus 3 of the fourth embodiment includes, in place of the control-signal input unit 36 of the communication apparatus shown in FIG. 3, an oscillator 50 that is connected to the RF transmitting unit 37 and generates the power supply signal and defines an oscillating frequency as shown in FIG. 5.

In the above described structure, when the capsule endoscope 2 receives an activating signal (power supply signal) which is oscillated by the communication apparatus 3 and has a predetermined frequency band, the electromotive force is generated in the coil 27a. When the voltage of the condenser 27c reaches a level equal to or above a predetermined level due to the generated electromotive force, the power supply IC 41 is activated to supply the power to the intra-capsule function executing circuit 40. Thus, the intra-capsule function executing circuit 40 is turned into a state in which the intra-capsule function executing circuit 40 can be activated.

As can be seen from the foregoing, in the fourth embodiment, after being introduced inside the subject, the capsule endoscope receives the power supply signal which is transmitted from the outside. Then, the power is supplied to the intra-capsule function executing circuit and the intra-capsule function executing circuit is controlled to be driven according to the power supply signal. Therefore, the time to start driving the capsule endoscope can be set to a time after the capsule endoscope is securely placed inside the subject, whereby the collection and the transmission of the image inside the subject can be performed appropriately.

Fifth Embodiment

Figure 9:
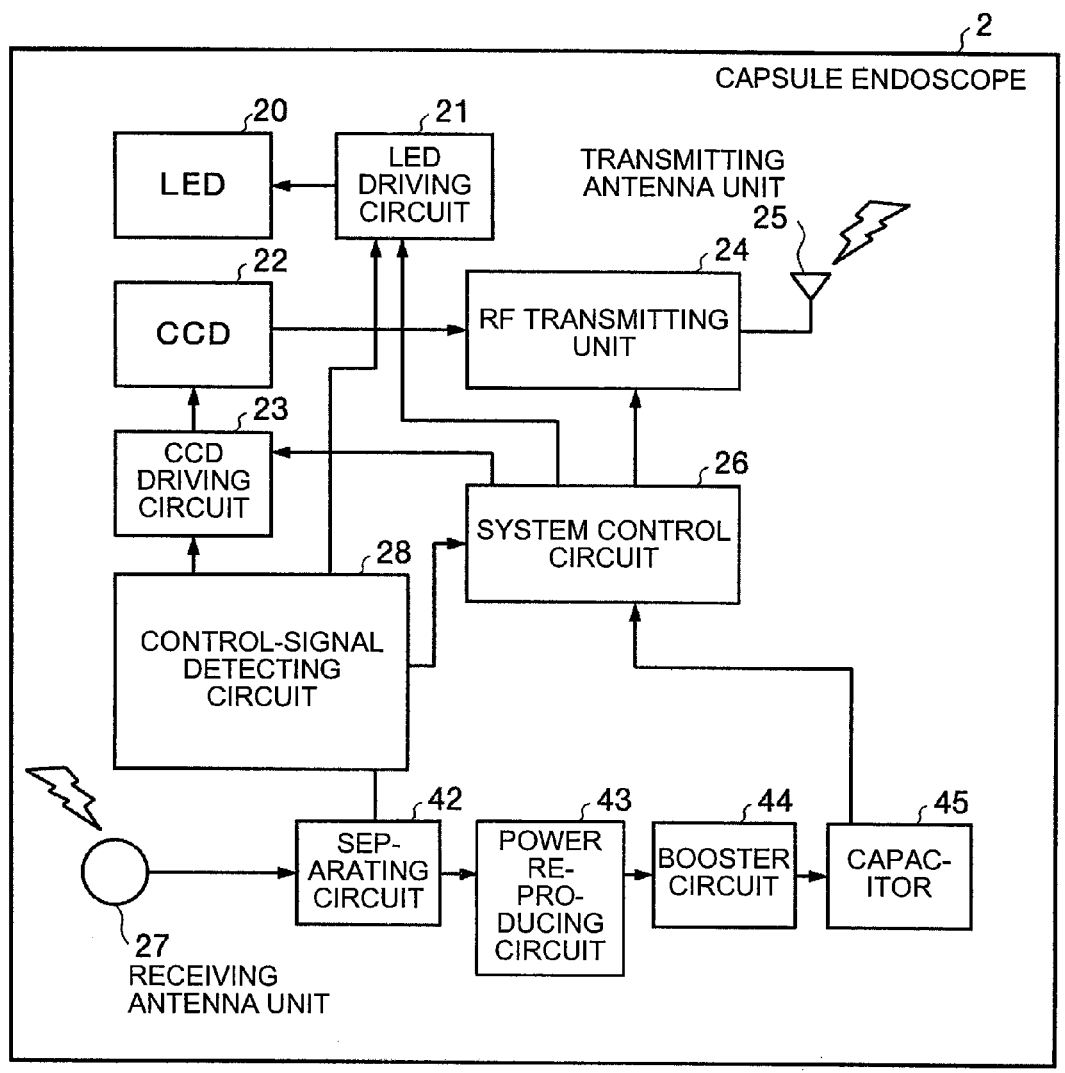
FIG. 9 is a block diagram of a fifth embodiment of the internal structure of the capsule endoscope shown in FIG. 1.
Figure 10:
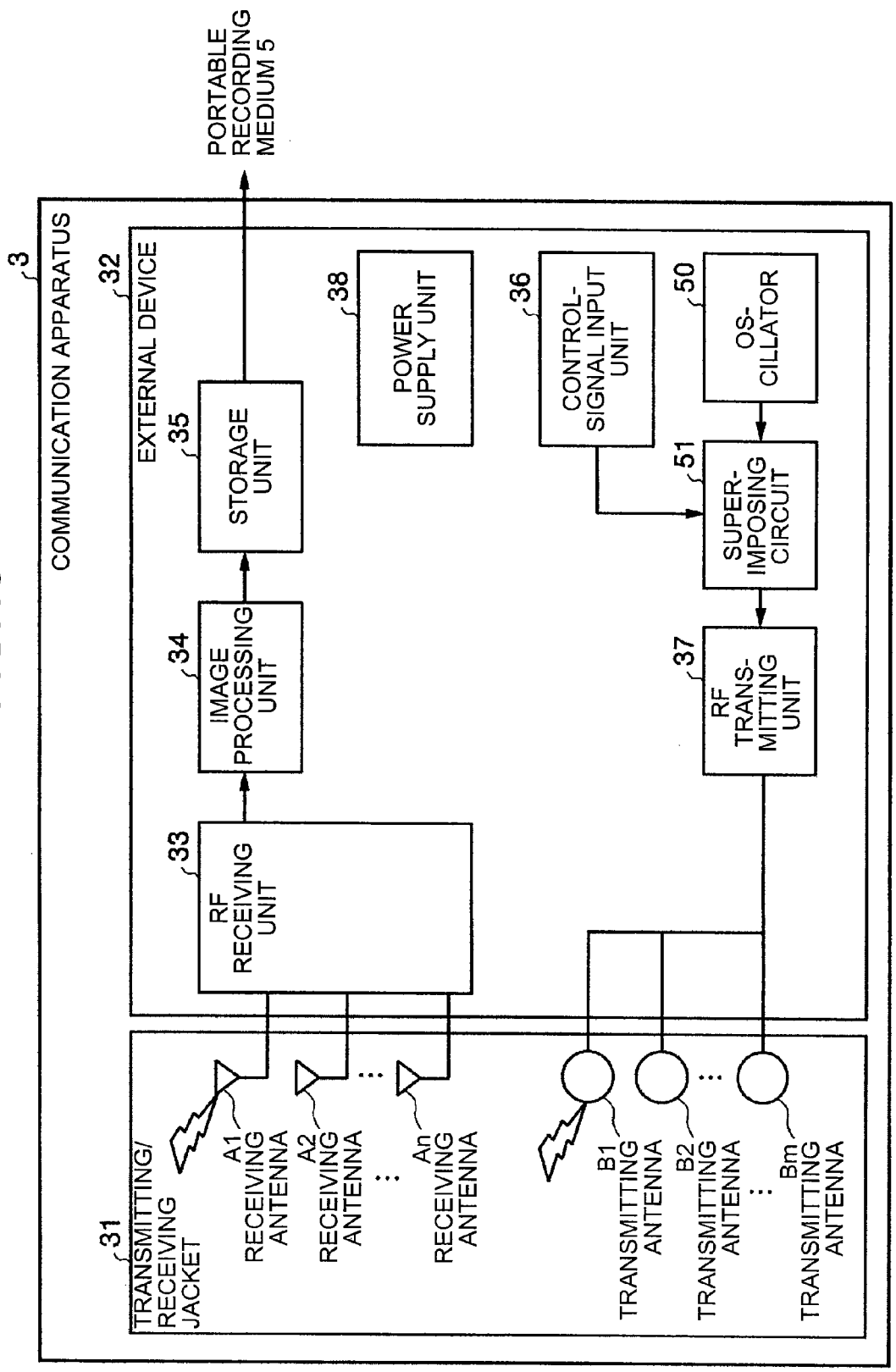
FIG. 10 is a block diagram of the fifth embodiment of the internal structure of the communication apparatus shown in FIG. 1.

FIGS. 9 and 10 are block diagrams of an internal structure of a capsule endoscope and a communication apparatus according to a fifth embodiment. In the fifth embodiment, the activating signal is superimposed on the power supply signal and the resulting signal is transmitted to the capsule endoscope 2 when the power is supplied to the capsule endoscope 2.

In FIG. 9, the capsule endoscope 2 includes the system control circuit 26, the receiving antenna unit 27, the control-signal detecting circuit 28, and the intra-capsule function executing circuit as shown in FIG. 2. Further, the capsule endoscope 2 includes a separating circuit 42 that separates the power supply signal from the signal received by the receiving antenna unit 27, a power reproducing circuit 43 that reproduces power from the separated power supply signal, a booster circuit 44 that boosts the reproduced power, and a capacitor 45 that stores boosted power. The control-signal detecting circuit 28 detects an activating signal whose input level is equal to or above a predetermined level from the components separated from the power supply signal in the separating circuit 42, and supplies a control signal to the system control circuit 26 according to the detection.

The system control circuit 26 includes a switch element, a latch circuit (not shown), and the like. These elements are connected between each element and the capacitor 45. On receiving the control signal (activating signal) from the control-signal detecting circuit 28, the latch circuit turns the switch element to an ON-state, and subsequently maintains the ON-state of the switch element to supply the driving power to the function executing circuit inside the capsule endoscope 2.

Further, the communication apparatus 3 includes, similarly to the communication apparatus of the first embodiment, the transmitting/receiving jacket 31, and the external device 32. The transmitting/receiving jacket 31 has the same structure as the structure of the jacket of the first embodiment. The external device 32, as shown in FIG. 10, includes the RF receiving unit 33, the image processing unit 34, the storage unit 35, the control-signal input unit 36, and the power supply unit 38. Further, the external device 32 includes the oscillator 50 that generates the power supply signal and defines the oscillating frequency, a superimposing circuit 51 that superimposes the activating signal output from the control-signal input unit on the power supply signal output from the oscillator 50 to combine the two signals, and the RF transmitting unit circuit 37 that converts the combined signal into radio frequency and outputs the result. In the external device 32, the signal acquired as a result of combining in the superimposing circuit 51 and the conversion in the RF transmitting unit 37 is transmitted to the transmitting antennas B1 to Bm and further transmitted to the capsule endoscope 2.

As can be seen from the foregoing, in the fifth embodiment, a combined signal of the power supply signal and the activating signal is transmitted from outside after the capsule endoscope is introduced inside the subject. The capsule endoscope receives and separates the combined signal, thereby detecting the activating signal. Then, the driving power stored in the capacitor is supplied to the intra-capsule function executing circuit based on the power supply signal. Thus, the driving of the intra-capsule function executing circuit is controlled. Therefore, the time to start driving the capsule endoscope can be set to a time after the capsule endoscope is surely placed inside the subject, and the collection and the transmission of the image inside the subject can be performed appropriately. Further, it is possible to store the power in the capacitor of the capsule endoscope substantially simultaneously with the supply of the driving power, in order to prevent the exhaustion of driving power.

Further, the timer function of the third embodiment may be provided to the fourth and the fifth embodiments, so that the power is supplied to the intra-capsule function executing circuit after the capsule endoscope is surely placed inside the organ to be examined. Still further, the control signal indicating the command to start activation employed in the third embodiment may be transmitted subsequent to the activating signal in the fourth and the fifth embodiments.

Still further, in the present invention, the activating signal may include only a signal of a predetermined radio frequency, and the activating signal may be transmitted to the capsule endoscope introduced inside the subject from the external device of the communication apparatus, so that the control-signal detecting circuit of the capsule endoscope detects the activating signal of the predetermined radio frequency. Such an arrangement can prevent the control-signal detecting circuit from making erroneous decision due to the presence of noise, and the collection and the transmission of the image of the object to be examined inside the subject can be performed more appropriately.

Sixth Embodiment

A wireless in-vivo information acquiring system (capsule-type communication system), a capsule endoscope (capsule-type medical apparatus), and a communication apparatus (biological information receiving apparatus) according to a sixth embodiment of the present invention will be described with reference to FIGS. 11 to 14.

Figure 11:
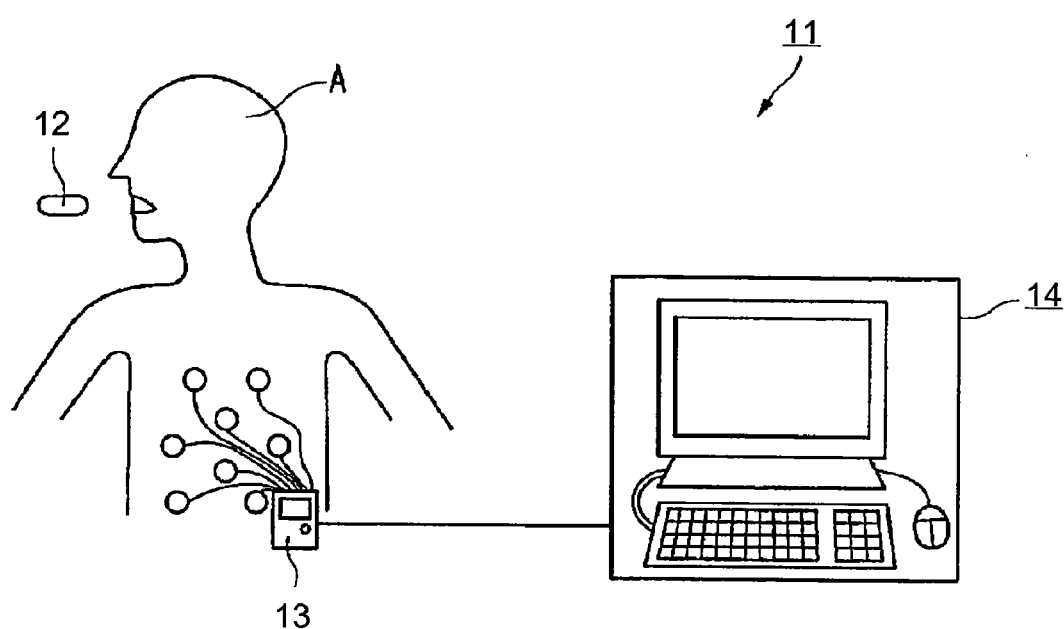
FIG. 11 is a schematic diagram of a wireless in-vivo information acquiring system according to a sixth embodiment of the present invention.

The wireless in-vivo information acquiring system 1 according to the sixth embodiment includes, as shown in FIG. 11, a capsule endoscope 12 that transmits in-vivo information (biological information) of a subject A from inside a body (inside the subject) to outside the body (outside the subject), a communication apparatus 13 that is arranged outside the body to receive image signals, i.e., in-vivo information, that are transmitted from the capsule endoscope 12, and a workstation 14 that serves to display image data recorded in the communication apparatus 13, and serves to detect the in-vivo information.

Further, the capsule endoscope 12 transmits a communication confirmation signal to confirm a communication status between the capsule endoscope 12 and the communication apparatus 13. The communication apparatus 13 transmits a communication permission signal to permit the transmission of the in-vivo information on receiving the communication confirmation signal. Further, the capsule endoscope 12 transmits the in-vivo information on receiving the communication permission signal. These signal transmission will be described later in detail.

The capsule endoscope 12 is swallowable by the subject A, and serves to acquire (detect) the in-vivo information while placed inside the subject A. In the sixth embodiment, images (image signals) inside the alimentary tract of the subject A will be described as the in-vivo information.

Figure 12:
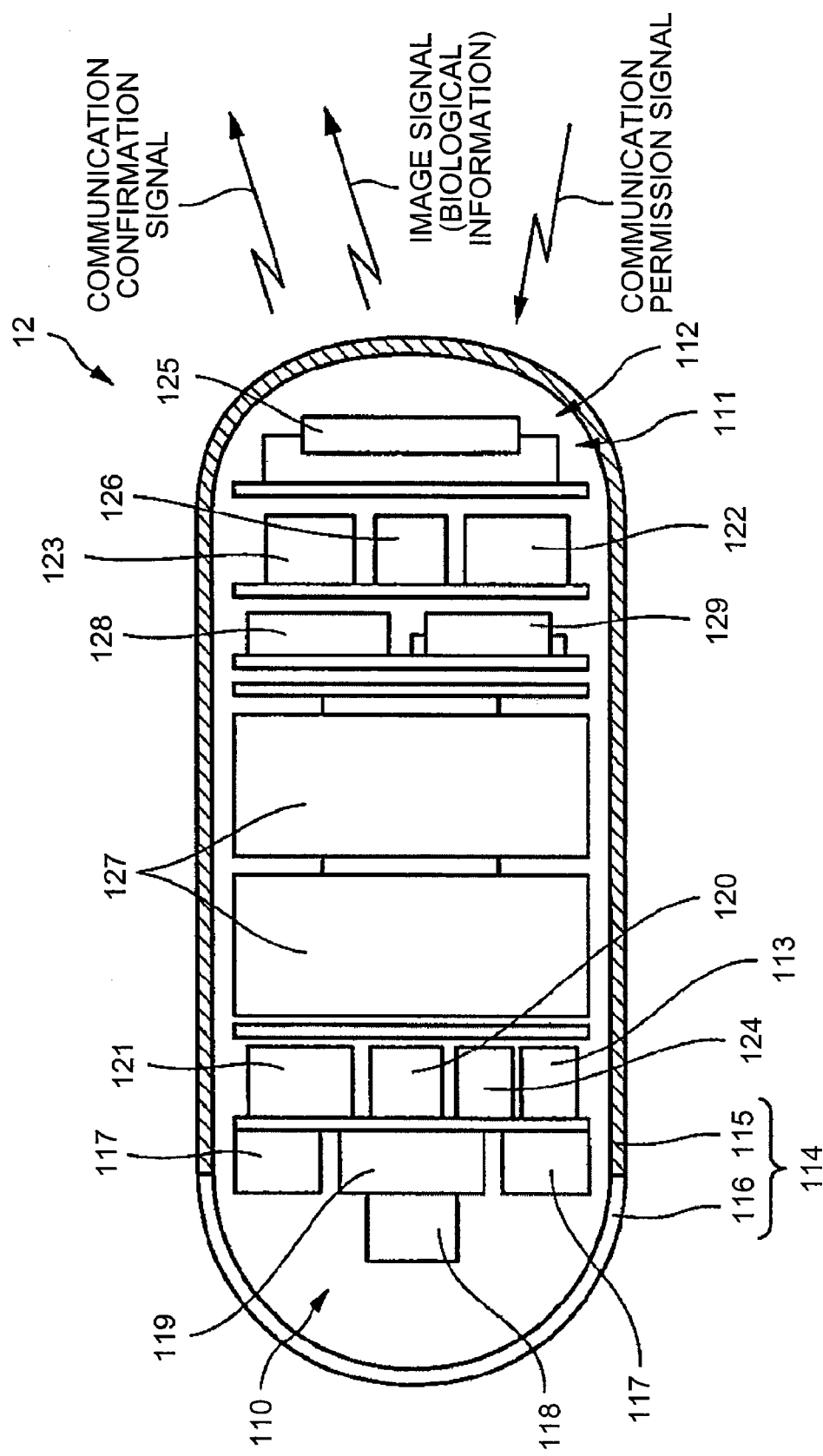
FIG. 12 is a sectional view of the capsule endoscope, which constitutes the wireless in-vivo information acquiring system shown in FIG. 11, according to the present invention.

The capsule endoscope 12 of the sixth embodiment includes, as shown in FIG. 12, an acquiring unit 110 that acquires images (in-vivo information), a transmitting unit 111 that transmits the acquired image and the communication confirmation signal to the communication apparatus 13, a receiving unit 112 that receives radio signals including at least the communication permission signal sent from the communication apparatus 13 in response to the communication confirmation signal, and a communication control unit (communication controller) 113 that determines whether to send the image or not based on a state of reception of the communication permission signal. Each of the above mentioned elements is incorporated inside an outer casing 114.

The outer casing 114 has a capsule-like casing 115 and a transparent cover 116 which is formed from a transparent member for image pick-up. Inside the outer casing 114, various elements are incorporated, such as an LED 117 that serves to illuminate an interior of the body, an objective lens 118 that focuses an intracorporeal image, i.e., that forms an image of a region to be observed inside the body, a solid-state imaging sensor 119 that captures the intracorporeal image, a memory 120 that stores the captured image, an imaging unit control unit 121 that controls the LED 117 and the solid-state imaging sensor 119, a modulator 122 that modulates image signals for transmission, a demodulator 123 that demodulates the communication permission signal which is a control signal transmitted from the communication apparatus 13 by radio, a signal processing circuit 124 that converts the image signals acquired by the solid-state imaging sensor 119 into a suitable form for transmission and performs predetermined processing on the communication permission signal, an antenna 125 that transmits/receives various types of signals to/from the communication control unit 113 and the communication apparatus 13, a switch 126 that switches connection so as to connect one of the modulator 122 and the demodulator 123 to the antenna 125, a battery 127 and a power supply circuit 128 that supply power to each of the elements mentioned above, and a power supply switch 129 that controls whether to operate the capsule endoscope 12 or not.

The LED 117, the objective lens 118, the solid-state imaging sensor 119, and the imaging unit control unit 121 form the acquiring unit 110. Further, the antenna 125, the switch 126, and the modulator 122 form the transmitting unit 111, whereas the antenna 125, the switch 126, and the demodulator 123 form the receiving unit 112. Further, as described above, both the transmitting unit 111 and the receiving unit 112 use the same antenna 125 according to the switching by the switch 126.

The objective lens 118 is provided inside the transparent cover 116. The solid-state imaging sensor 119 such as a CCD imager is arranged at a focusing position of the objective lens 118. Further, the plural LEDs 117 of white color, for example, are arranged around the objective lens 118 as the illuminating elements. Further, the solid-state imaging sensor 119 converts the image formed by the objective lens 118 into electronic signals. The image captured by the solid-state imaging sensor 119 is subjected to the predetermined processing such as image processing by the signal processing circuit 124, sent to the modulator 122 (arranged at a back portion of the capsule endoscope 12), and transmitted from the antenna 125.

The antenna 125 serves also as a receiving antenna that receives the communication permission signal which is a control signal sent from the communication apparatus 13. When the capsule endoscope 12 and the communication apparatus 13 have a good communication status therebetween, the communication permission signal sent from the communication apparatus 13 to the capsule endoscope 12 is received by the antenna 125. The received communication permission signal is demodulated by the demodulator 123 and the demodulated signal is transmitted to the communication control unit 113. Thereafter, the communication control unit 113 recognizes the transmitted communication permission signal and determines whether to transmit the image or not based on the results of recognition, thereby controlling the transmitting unit 111.

Figure 13:
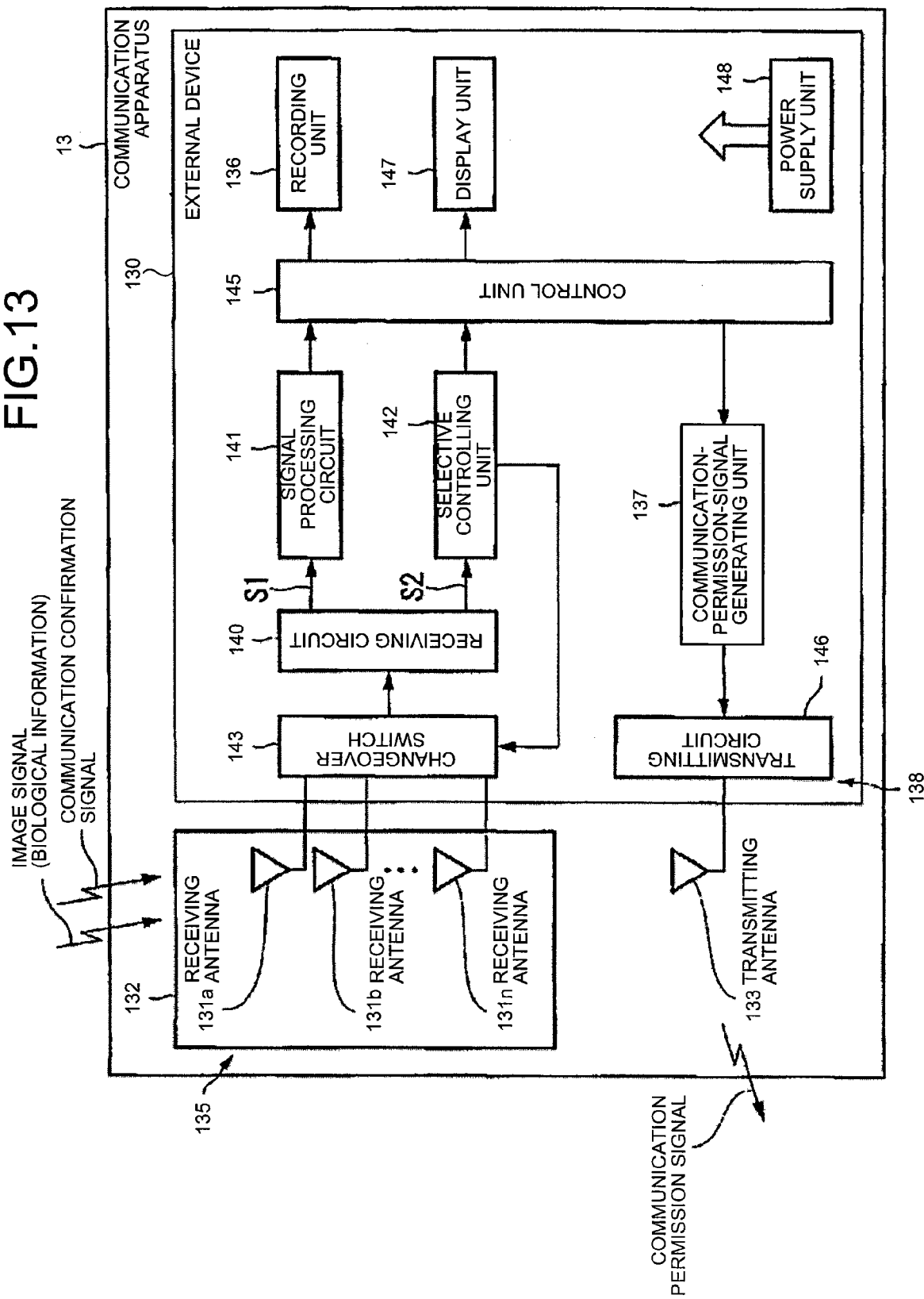
FIG. 13 is a block diagram of a structure of the communication apparatus, which constitutes the wireless in-vivo information acquiring system shown in FIG. 11, according to the present invention.

The communication apparatus 13, as shown in FIG. 13, includes an external device 130 that performs various types of processing such as demodulation and recording of each signal (image signal or communication confirmation signal) transmitted from the capsule endoscope 12, a receiving antenna unit 132 that has plural receiving antennas 131a, 131b, . . . for receiving each signal, and a transmitting antenna 133 that serves to transmit the communication permission signal.

Further, the communication apparatus 13 of the sixth embodiment includes a receiving unit 135 that receives the image signal (in-vivo information) and the communication confirmation signal, a recording unit 136 that records the received image signal, a communication-permission-signal generating unit 137 that generates the communication permission signal to permit the capsule endoscope 12 to transmit the in-vivo information when the receiving unit 135 receives the communication confirmation signal, and a communication permission signal transmitting unit 138 that transmits the generated communication permission signal.

Each signal received by the receiving antenna unit 132 is demodulated by a receiving circuit 140. The receiving circuit 140 provides a demodulated output S1 as an output, which is transmitted to a signal processing circuit 141 for processing corresponding to the type of the signal. Further, the receiving circuit 140 supplies a reception intensity signal S2 as an output, which is sent to a selective control unit 142. The selective control unit 142 compares the intensity of signals received at the respective receiving antennas 131a, 131b, . . . , 131n based on the reception intensity signals S2, and selects an antenna which is most suitable for the reception. Then, the selective control unit 142 controls a changeover switch 143 to perform actual antenna switching based on the result of selection.

When the signal received by the receiving antenna unit 132 is an image signal sent from the capsule endoscope 12, the signal is subjected to various types of processing such as image data correction and compression by the signal processing circuit 141, and the processed image data is recorded in the recording unit 136 via a control unit 145. The recording unit 136 is, for example, a portable recording medium.

On the other hand, when the signal received by the receiving antenna unit 132 is a communication confirmation signal sent from the capsule endoscope 12, after recognizing the communication confirmation signal, the control unit 145 commands the communication-permission-signal generating unit 137 to generate a communication permission signal to permit the capsule endoscope 12 to transmit the image signal. The communication permission signal generated by the communication-permission-signal generating unit 137 is modulated in a transmitting circuit 146 and the resulting modulated signal is transmitted from the transmitting antenna 133.

Further, various types of information such as information related to the subject A (patient) and error information are displayed on a display unit 147 and the workstation 14 under the control of the control unit 145. Further, a power supply unit 148 supplies necessary power for each functional block of the communication apparatus 13.

The receiving circuit 140, the signal processing circuit 141, the selective control unit 142, the changeover switch 143, the control unit 145, the recording unit 136, the communication-permission-signal generating unit 137, the transmitting circuit 146, the display unit 147, and the power supply unit 148 form the external device 130.

Further, the receiving antenna unit 132, the changeover switch 143, and the receiving circuit 140 form the receiving unit 135, whereas the transmitting antenna 133 and the transmitting circuit 146 form the communication permission signal transmitting unit 138.

Figure 14A:
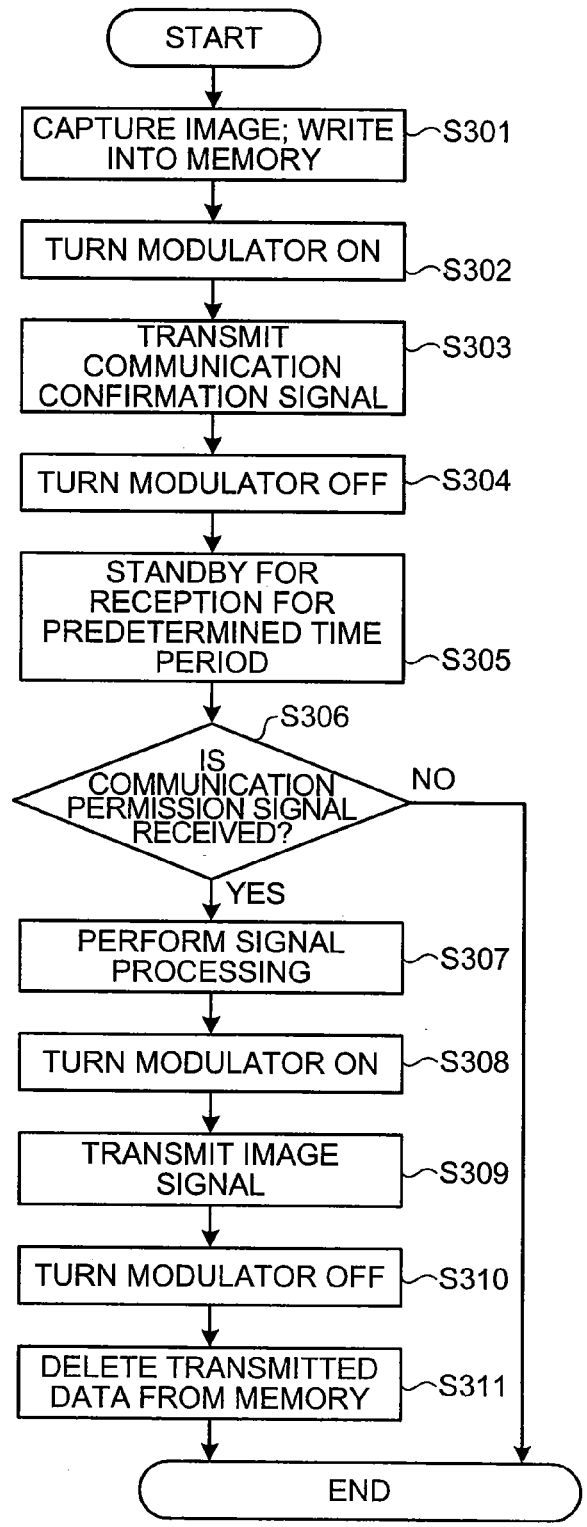
FIG. 14A is a flowchart illustrating a communication procedure of the capsule endoscope in which in-vivo information of a subject is acquired by the wireless in-vivo information acquiring system shown in FIG. 11.
Figure 14B:
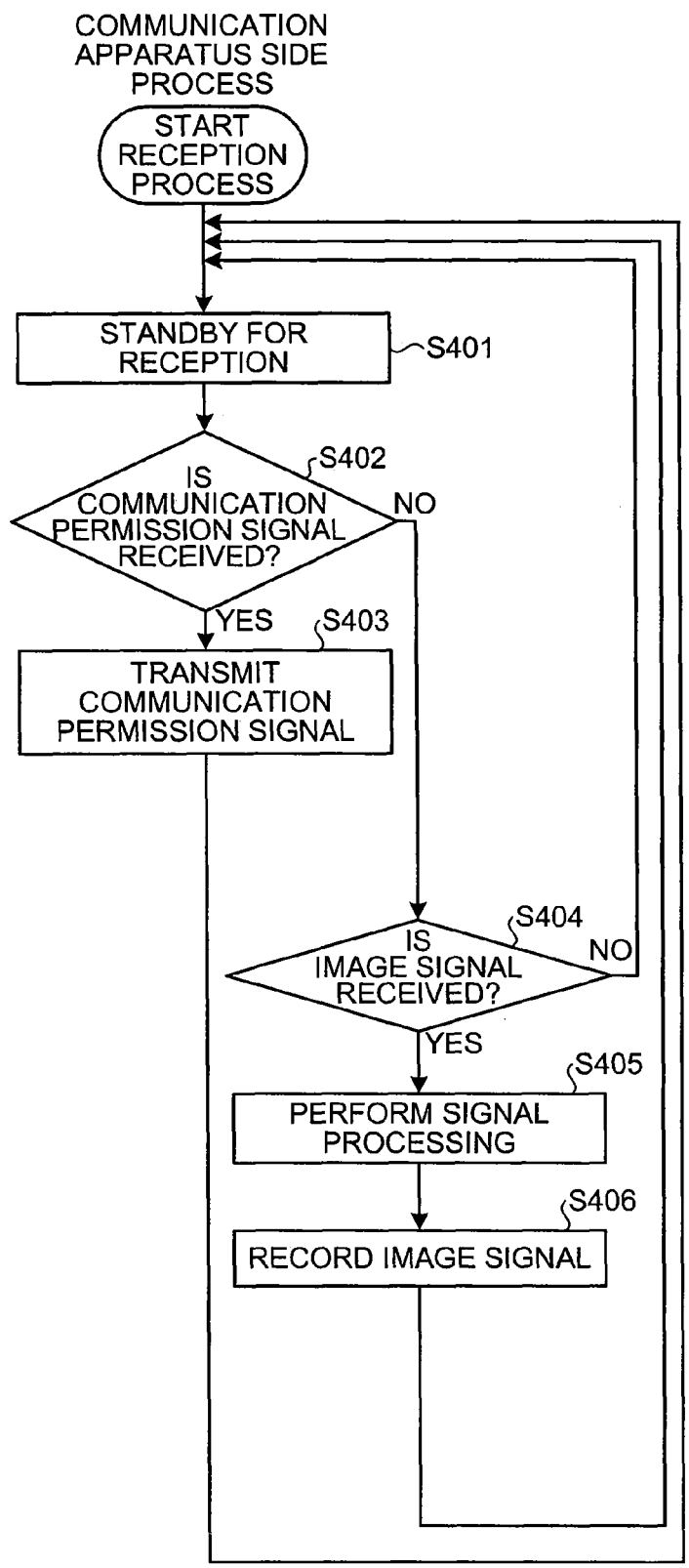
FIG. 14B is a flowchart illustrating a communication procedure of the communication apparatus in which the in-vivo information of a subject is acquired.

A manner of acquisition of the in-vivo information of the subject A by the wireless in-vivo information acquiring system 11 having the above described structure, more specifically, the acquisition of the image inside the alimentary tract will be described with reference to FIGS. 14A and 14B.

The capsule endoscope 12 when placed inside the subject A performs an imaging operation with a timing determined by the imaging unit control unit 121, and writes the image data acquired by imaging into the memory 120 (S301). Thereafter, the capsule endoscope 12 turns the modulator 122 on (S302), and transmits the communication confirmation signal to determine whether the communication status between the capsule endoscope 12 and the communication apparatus 13 is good or not (S303). Since the intensity of the communication confirmation signal is substantially equal to the intensity of the transmitted image signal, the communication apparatus 13 determines that the communication apparatus 13 can receive the image signal if it can receive the communication confirmation signal. Preferably, the communication confirmation signal has a fixed pattern, and can be distinguished from exogenous noises received by the communication apparatus 13. The form of the communication confirmation signal is not limited thereto, however, and the communication confirmation signal may be a non-modulated signal, for example, and the communication apparatus 13 may determine whether the sent signal is the communication confirmation signal or not by checking the intensity of the received signal. After the transmission of the communication confirmation signal, the modulator 122 is turned off (S304).

On the other hand, the communication apparatus 13 is in a standby state for reception until the communication confirmation signal or the image signal is received (S401). If the communication apparatus 13 receives the communication confirmation signal during standby (Yes in S402), the communication apparatus 13 transmits the communication permission signal to the capsule endoscope 12 (S403). Here, similarly to the communication confirmation signal, it is preferable that the communication permission signal have a fixed pattern and can be distinguished from the exogenous noise. The form of the communication permission signal is, however, not limited thereto. After transmitting the communication permission signal, the communication apparatus 13 is turned back to the standby state for reception (S401).

Further, after transmitting the communication confirmation signal (S303), the capsule endoscope 12 assumes a standby state for a predetermined time period which is long enough for the communication apparatus to send back the communication permission signal (S305). If the capsule endoscope 12 receives the communication permission signal during this period (Yes in S306), the communication control unit 113 determines whether to transmit the image signal or not. If the communication control unit 113 determines to transmit the image signals, the communication control unit 113 controls the transmitting unit 111 for transmission. Specifically, the image data stored in the memory 120 is converted into transmitted image data which is more suitable for the transmission by the signal processing circuit 124 (S307), and at the same time, the modulator 122 is turned on under the control of the signal processing circuit 124 (S308). Then, the transmitted image data is modulated by the modulator 122 and the modulated image data is transmitted from the antenna 125 (S309). After the transmission of the transmitted image data, the modulator 122 is turned off again (S310) and the image data in the memory 120 is deleted (S311).

On the other hand, if the capsule endoscope 12 does not receive the communication permission signal within the set period (No in S306), the modulator 122 remains off and waits until the next imaging time comes.

When the capsule endoscope 12 transmits the image signal (S309), the communication apparatus 13 receives the image signal by the receiving unit 112 (Yes in S404), the signal processing circuit 124 performs predetermined processing such as image compression (S405), and the processed data is recorded in the recording unit 136 (S406), and also displayed on the display unit 147 and the workstation 14. The amount of the image to be stored in the memory 120 of the capsule endoscope 12 is not limited to one frame. It is possible to record plural frames of images in the memory 120 and to sequentially transmit the plural frames of image data after the communication permission signal is confirmed. A doctor or the like can make diagnosis on, for example, a health condition of the subject A by looking at the displayed image or the image recorded in the recording unit 136.

As described above, with the wireless in-vivo information acquiring system 11, the capsule endoscope 12, and the communication apparatus 13 according to the sixth embodiment, the image signals, i.e., the in-vivo information can be transmitted and received when the capsule endoscope 12 and the communication apparatus 13 have a good communication status therebetween. Specifically, the capsule endoscope 12 transmits the communication confirmation signal before transmitting the image signal. When the communication apparatus 13 receives the communication confirmation signal, in other words, when the capsule endoscope 12 and the communication apparatus 13 have a good communication status therebetween, the communication apparatus 13 sends the communication permission signal to permit to send the image signal. Since the capsule endoscope 12 transmits the image signal only after receiving the communication permission signal, the capsule endoscope 12 can surely transmits the image signal to the communication apparatus 13. Therefore, the capsule endoscope 12 does not send the image data (image signals) to the communication apparatus 13 when the communication apparatus 13 is unable to receive the image signals, whereby there is no waste in power consumption.

Further, since the communication apparatus 13 can securely acquire the image signals, there is no missing in the acquired images as in the conventional system (due to mal communication). Thus, the diagnosis of, for example, the health condition of the subject A can be surely performed.

Still further, if the system is configured so that the plural frames of image data are stored in the memory 120 and the plural frames are collectively transmitted when the communication permission signal is received, it is possible to reduce the number of image frames that are not received by the communication apparatus 13 though transmitted from the capsule endoscope 12.

Seventh Embodiment

Figure 16:
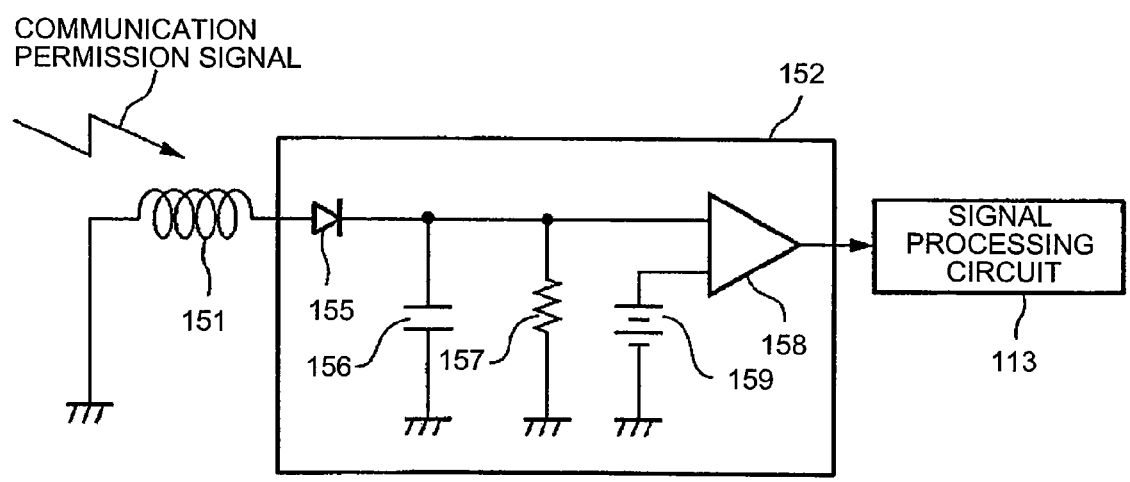
FIG. 16 is a circuit diagram of a portion around a receiving antenna in the capsule endoscope of FIG. 15.

A seventh embodiment of the capsule endoscope according to the present invention will be described with reference to FIGS. 15 and 16. When the element of the seventh embodiment is the same as the element of the sixth embodiment, the same reference character will be allocated thereto and the description thereof will not be repeated.

The seventh embodiment is different from the sixth embodiment in that a capsule endoscope 150 of the seventh embodiment includes the receiving unit 112 which has a separate coil-like antenna 151 that receives the communication permission signal, while the capsule endoscope 12 of the sixth embodiment has the shared antenna 125 for the reception of the communication permission signal. Specifically, the capsule endoscope 150 of the seventh embodiment, as shown in FIGS. 15 and 16, includes inside the outer casing 114, the coil-like antenna 151, and a received signal detecting circuit (envelope detecting circuit) 152 that serves to detect the communication permission signal from the signals received by the coil-like antenna 151.

An operation of the received signal detecting circuit 152 when the capsule endoscope 150 having the above described structure receives the communication permission signal from the communication apparatus 13 will be described with reference to FIG. 16. When the communication permission signal is sent, a potential is generated based on the ground of the coil-like antenna 151 as a reference. When a sufficient potential difference is generated between two ends of a diode 155, the diode 155 is turned on, and electric charges start to be accumulated in a condenser 156. A resistor 157 serves to let the accumulated electric charges out of the condenser 156. Therefore, the potential of the upper end of the condenser 156 rises according to a time constant determined by the values of the resistor 157 and the condenser 156. Further, a comparator 158 compares the potential of the upper end of the condenser 156 with the reference potential generated by a reference voltage generator 159. Therefore, the communication permission signal can be detected based on the output from the comparator 158.

As described above, since the capsule endoscope 150 of the seventh embodiment includes the received signal detecting circuit 152 which is formed primarily from passive elements, the power consumption can be suppressed to a low level. In addition, since the number of elements is small, the capsule endoscope 150 can be formed in a small size.

Further, in the seventh embodiment, the communication permission signal sent from the communication apparatus 13 can be made smaller than the communication confirmation signal sent from the capsule endoscope 150. For example, the communication permission signal can be made to approximately a few tens KHz. When the signal of such a low frequency is employed, the attenuation of the signal while the signal is passing through the body can be suppressed to a low level.

Eighth Embodiment

An eighth embodiment of the capsule endoscope and the communication apparatus according to the present invention will be described with reference to FIGS. 17 to 18. Common elements between the eighth embodiment and the sixth and the seventh embodiments will be denoted by the same reference characters and the description thereof will not be repeated.

The eighth embodiment is different from the sixth embodiment in that a capsule endoscope 160 of the eighth embodiment operates by receiving power from the communication apparatus 13 by radio, while the capsule endoscope 12 of the sixth embodiment operates by the incorporated battery 127. Specifically, the capsule endoscope 160 of the eighth embodiment includes the receiving unit 112 which has a coil-like antenna 161 for receiving power sent from outside the body and a power receiving unit 162, as shown in FIGS. 17 and 18.

In the eighth embodiment, the communication permission signal functions also as a power supply signal (radio signal) that serves to supply power to the capsule endoscope 160. The power may be supplied in other manners. For example, a power supply unit may be arranged outside the body, and power may be supplied to the capsule endoscope 160 from the power supply unit by radio. Alternatively, the communication apparatus 13 may serve also as a power supply unit and a power supply signal may be transmitted separately from the communication permission signal from the transmitting antenna 133.

As shown in FIG. 18, the power receiving unit 162 includes a rectifying circuit 163 that serves to acquire power from the communication permission signal, and a communication permission detecting unit 164 that detects the communication permission signal from the output of the rectifying circuit 163 to send the detected communication permission signal to the communication control unit 113. The rectifying circuit 163 has the same structure as the received signal detecting circuit 152 of the seventh embodiment.

An operation of the power receiving unit 162 when the capsule endoscope 160 having the above described structure receives the communication permission signal from the communication apparatus 13 will be described with reference to FIG. 18. The communication permission signal (which serves also as a power supply signal) transmitted from the communication apparatus 13 is converted into a voltage by the coil-like antenna 161 and rectified by the rectifying circuit 163. The communication permission detecting unit 164 determines whether the communication permission signal is sent or not based on the output from the rectifying circuit 163, and transmits the result of determination to the communication control unit 113. Only when the communication permission signal is detected, the communication control unit 113 operates the signal processing circuit 124 and the modulator 122 to transmit the image signals. The output from the rectifying circuit 163 is temporarily accumulated in an accumulating unit 165 and stabilized by a power supply circuit 166. Thereafter the stabilized output is supplied to each element.

As described above, since the capsule endoscope 160 of the eighth embodiment can receive the supply of power via the communication permission signal, power exhaustion, such as battery exhaustion can be prevented. Therefore, regardless of the life of the battery and the like, the image inside the body, i.e., the in-vivo information can be surely acquired. Further, since the communication permission detecting unit 164 detects the communication permission signal from the output of the rectifying circuit 163, there is no need of providing a separate detecting circuit. Therefore, the structure of the capsule endoscope can be simplified and downsized. Specifically, since the communication permission signal functions also as the radio signal to supply power, only a single transmitting unit is sufficient, whereby the communication apparatus 13 can be readily configured and downsized.

Here, the capsule endoscope 160 of the eighth embodiment operates by receiving power from outside. Therefore, if the communication apparatus 13 does not receive the communication confirmation signal from the capsule endoscope 160, there can be two reasons. Firstly, the communication status is not good. Secondly, the capsule endoscope 160 is not operating due to shortage of power.

In order to prevent the power shortage of the capsule endoscope 160, it may be preferable to set the communication permission signal transmitting unit 138 so that the communication permission signals are sent at longer intervals than the intervals of the transmission of the communication confirmation signals from the capsule endoscope 160 while the communication confirmation signal is not received. Then, the power can be supplied to the capsule endoscope 160 as appropriate, and the power exhaustion would not obstruct the transmission of the communication confirmation signal. Such arrangement can lead to a secure acquirement of an intra-subject image.

INDUSTRIAL APPLICABILITY

The wireless in-vivo information acquiring apparatus and the wireless in-vivo information acquiring system according to the present invention are useful for the medical observation apparatus that is introduced inside the human body and employed for an observation of an examined region, and more particularly, suitable for securely performing the collection and the transmission of the intra-subject image by starting the driving of the medical observation apparatus at a previously set time.

The invention claimed is:

1. A wireless in-vivo information acquiring apparatus that detects in-vivo information of a subject and transmits the in-vivo information to a communication apparatus located outside the subject, the wireless in-vivo information acquiring apparatus comprising:
   an acquiring unit that acquires the in-vivo information;
   a transmitting unit that transmits the in-vivo information acquired, and generates a communication confirmation signal to transmit to the communication apparatus, the communication confirmation signal serving to confirm a communication status between the wireless in-vivo information acquiring apparatus and the communication apparatus;
   a receiving unit that receives a radio signal which is sent from the communication apparatus in response to the communication confirmation signal and which includes at least a communication permission signal; and
   a communication controller that determines whether to transmit the in-vivo information or not based on a state of reception of the communication permission signal.

2. The wireless in-vivo information acquiring apparatus according to claim 1, wherein
   the transmitting unit and the receiving unit share a same antenna.

3. The wireless in-vivo information acquiring apparatus according to claim 1, wherein
   the receiving unit includes an envelope detecting circuit.

4. The wireless in-vivo information acquiring apparatus according to claim 1, wherein
   the receiving unit includes
      a rectifying circuit that serves to acquire power from the radio signal, and
      a communication permission detector that detects the communication permission signal from an output of the rectifying circuit and sends the communication permission signal to the communication controller.

5. A wireless in-vivo information acquiring system, comprising:
   a wireless in-vivo information acquiring apparatus which is introduced into a subject; and
   a communication apparatus which is arranged outside the subject and acquires information acquired by the wireless in-vivo information acquiring apparatus through radio communication, wherein
   the wireless in-vivo information acquiring apparatus includes
      a function executing unit that executes a predetermined function in the subject into which the wireless in-vivo information acquiring apparatus is introduced,
      a first radio receiving unit that is configured to receive a radio signal from outside the subject, and
      an activating unit configured to determine that an input of control signals is discontinued when an intensity level of a control signal received by the first radio receiving unit becomes equal to or lower than a predetermined level and to control an activation of the function executing unit according to a discontinuation in an input of the control signals, and
   the communication apparatus includes
      a second radio receiving unit that receives the information transmitted through radio communication, and
      a radio transmitting unit that transmits the control signal of a predetermined output level through radio communication, the predetermined output level comprising:
         an output level set to be detected as an intensity level of the control signals received by the second radio receiving unit which is higher than the predetermined level before the wireless in-vivo information acquiring apparatus is introduced into the subject, and
         the output level to be detected as an intensity level of the control signals attenuated by the subject and received by the second radio receiving unit which is equal to or lower than the predetermined level after the wireless in-vivo information acquiring apparatus is introduced into the subject.

6. The wireless in-vivo information acquiring system according to claim 5, wherein
   the activating unit determines that the input of the control signals is discontinued when an input level of the control signal from the first radio receiving unit is equal to or lower than a predetermined level, to control the activation of the function executing unit.

7. The wireless in-vivo information acquiring system according to claim 5, wherein
   the radio transmitting unit of the communication apparatus transmits the control signal that is within a predetermined frequency band,
   the first radio receiving unit of the wireless in-vivo information acquiring apparatus receives the control signal within the predetermined frequency band from outside the subject, and the activating unit determines that the input of the control signals is discontinued when an input level of the control signal that is within the predetermined frequency band and received by the first radio receiving unit is equal to or lower than a predetermined level, to control the activation of the function executing unit.

8. The wireless in-vivo information acquiring system according to claim 5, wherein
the activating unit activates the function executing unit after a predetermined time passes since the discontinuation in the input of the control signals.

9. The wireless in-vivo information acquiring system according to claim 5, wherein
the activating unit performs a control such that the function executing unit keeps being driven regardless of the presence/absence of the control signals input after the function executing unit starts to be driven.

10. The wireless in-vivo information acquiring system according to claim 5, wherein
the communication apparatus halts the transmission of the control signals after a predetermined time period passes since the transmission starts.

11. The wireless in-vivo information acquiring system according to claim 5, wherein
the communication apparatus halts the transmission of the control signals when the communication apparatus receives the image data transmitted from the wireless in-vivo information acquiring apparatus.

12. A wireless in-vivo information acquiring system, comprising:
a wireless in-vivo information acquiring apparatus that is introduced inside a subject; and
a communication apparatus that is arranged outside the subject and acquires information acquired by the wireless in-vivo information acquiring apparatus by radio communication, wherein
the wireless in-vivo information acquiring apparatus includes
a function executing unit that executes a predetermined function inside the subject in which the wireless in-vivo information acquiring apparatus is introduced,
a first radio receiving unit that is configured to receive a radio signal from outside the subject,
a power reproducing unit that separates a power supply signal from the radio signal received by the first radio receiving unit, reproduces power from the separated power supply signal and supplies the reproduced power to the function executing unit, and
an activating unit that controls an activation of the function executing unit according to an input of an activating signal obtained by separating the power supply signal from the radio signal received by the first radio receiving unit, and
the communication apparatus includes
a second radio receiving unit that receives the information transmitted through radio communication, and
a first radio transmitting unit that transmits a resultant signal including the activating signal superimposed on the power supply signal through radio communication.

13. The wireless in-vivo information acquiring system according to claim 12, wherein
the activating unit controls the activation of the function executing unit based on an input level of the activating signal received by the first radio receiving unit.

14. The wireless in-vivo information acquiring system according to claim 12, wherein
the activating unit controls the activation of the function executing unit according to an input of a signal that indicates a command to start activation and that is received by the first radio receiving unit.

15. The wireless in-vivo information acquiring system according to claim 12, wherein
the activating unit activates the function executing unit after a predetermined time passes since the signal is input.

16. A wireless in-vivo information acquiring system, comprising:
a wireless in-vivo information acquiring apparatus that transmits in-vivo information of a subject from inside the subject to outside the subject; and
a communication apparatus that is located outside the subject and receives the in-vivo information, the wireless in-vivo information acquiring system detecting the in-vivo information, wherein
the wireless in-vivo information acquiring apparatus generates and transmits a communication confirmation signal to confirm a communication status between the wireless in-vivo information acquiring apparatus and the communication apparatus,
the communication apparatus, on receiving the communication confirmation signal, transmits a communication permission signal to permit communication, and
the wireless in-vivo information acquiring apparatus includes a communication controller that transmits the in-vivo information on receiving the communication permission signal.

17. The wireless in-vivo information acquiring system according to claim 16, wherein
the communication permission signal also serves as a radio signal for supplying power to the wireless in-vivo information acquiring apparatus.

18. A communication apparatus that is located outside a subject to receive in-vivo information which is transmitted from a wireless in-vivo information acquiring apparatus inside the subject, and to receive a communication confirmation signal which serves to confirm a communication status between the communication apparatus and the wireless in-vivo information acquiring apparatus, the communication apparatus comprising:
a receiving unit that receives the in-vivo information and the communication confirmation signal;
a recording unit that records the in-vivo information received;
a communication permission signal generator that generates a communication permission signal for permitting the wireless in-vivo information acquiring apparatus to transmit the in-vivo information, when the receiving unit receives the communication confirmation signal; and
a communication permission signal transmitting unit that transmits the communication permission signal.

19. The communication apparatus according to claim 18, wherein
the communication permission signal also serves as a radio signal for supplying power to the wireless in-vivo information acquiring apparatus.

20. The communication apparatus according to claim 19, wherein
the communication permission signal transmitting unit transmits the communication permission signal at a longer interval than an interval of transmission of the communication confirmation signals from the wireless in-vivo information acquiring apparatus, while the communication confirmation signal is not received.

* * * * *